United States Patent
Lund et al.

(10) Patent No.: US 12,199,378 B2
(45) Date of Patent: *Jan. 14, 2025

(54) MODULAR PATIENT MONITORING MEDICAL DEVICE AND CONNECTOR

(71) Applicant: Drägerwerk AG & Co. KGaA, Lübeck (DE)

(72) Inventors: Peter A. Lund, Nashua, NH (US); Andrew T. Provencher, Lowell, MA (US); Taylor Scott George, Amherst, NH (US); John C. Magill, Woburn, MA (US)

(73) Assignee: Drägerwerk AG & Co. KGaA (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/211,979

(22) Filed: Jun. 20, 2023

(65) Prior Publication Data

US 2023/0335951 A1 Oct. 19, 2023

Related U.S. Application Data

(63) Continuation of application No. 17/045,759, filed as application No. PCT/EP2019/058855 on Apr. 8, 2019, now Pat. No. 11,721,939.

(Continued)

(51) Int. Cl.
*H01R 13/64* (2006.01)
*A61B 5/00* (2006.01)
(Continued)

(52) U.S. Cl.
CPC ............. *H01R 13/64* (2013.01); *A61B 5/742* (2013.01); *H01R 13/50* (2013.01);
(Continued)

(58) Field of Classification Search
CPC ...... H01R 13/6581–6597; H01R 13/64; H01R 13/50; H01R 13/5219; H01R 2201/12; A61B 5/742
(Continued)

(56) References Cited

U.S. PATENT DOCUMENTS

| | | | | |
|---|---|---|---|---|
| 2,655,638 A * | 10/1953 | Allen | ................... | H01R 13/523 439/502 |
| 4,355,855 A * | 10/1982 | Rebikoff | .............. | H01R 13/523 439/445 |
| 7,201,612 B1 * | 4/2007 | Hou | ..................... | H01R 13/052 439/678 |
| 8,460,016 B2 * | 6/2013 | Liu | ........................ | H01R 31/06 439/106 |

(Continued)

*Primary Examiner* — Gary F Paumen
(74) *Attorney, Agent, or Firm* — Design IP

(57) ABSTRACT

Systems, methods, devices, and connectors are described herein for a modular patient monitoring medical device. A new generation of physiological measurement devices, such as Intelligent Patient Front End Devices (IPFE) can provide updated algorithms, features, and software updates for parameter measurement devices without corresponding releases of a new version of host monitor software. IPFEs, together with patient sensors, comprise a complete physiological patient parameter measurement delivery system. A number and a type of parameter measurement devices can be configured to meet varied and changing clinical needs. Remote access to versions, logs, self-tests, settings, history, and/or measurements via the Internet to one or more parameter measurement devices can provide a unified service approach. The connector is configured to electrically connect any two or more devices and provides an electrical connection that can be simply physically or tactually confirmed.

19 Claims, 25 Drawing Sheets

Related U.S. Application Data

(60) Provisional application No. 62/786,047, filed on Dec. 28, 2018, provisional application No. 62/654,215, filed on Apr. 6, 2018.

(51) Int. Cl.
  *H01R 13/50* (2006.01)
  *H01R 13/52* (2006.01)
  *H01R 13/6583* (2011.01)

(52) U.S. Cl.
  CPC ...... *H01R 13/5219* (2013.01); *H01R 13/6583* (2013.01); *H01R 2201/12* (2013.01)

(58) Field of Classification Search
  USPC ....... 439/205, 206, 607.01–607.58, 274, 275
  See application file for complete search history.

(56) References Cited

U.S. PATENT DOCUMENTS

| | | | | |
|---|---|---|---|---|
| 8,827,731 | B2* | 9/2014 | Sasaki | H01R 13/46 |
| | | | | 439/206 |
| 8,961,209 | B2* | 2/2015 | Kobayashi | H01M 50/503 |
| | | | | 439/378 |
| 8,961,235 | B2* | 2/2015 | Little | H01R 13/64 |
| | | | | 439/660 |
| 11,721,939 | B2* | 8/2023 | Lund | H01R 24/20 |
| | | | | 439/607.17 |
| 2009/0305558 | A1* | 12/2009 | Scholler | H01R 13/5025 |
| | | | | 439/569 |
| 2013/0065432 | A1* | 3/2013 | Fu | H01R 13/748 |
| | | | | 439/569 |
| 2014/0094060 | A1* | 4/2014 | Metzler | H01R 13/6215 |
| | | | | 439/569 |

* cited by examiner

MODULAR PATIENT MONITORING MEDICAL DEVICE AND CONNECTOR

CROSS-REFERENCE TO RELATED APPLICATIONS

This application is a continuation of U.S. patent application Ser. No. 17/045,759, filed on Oct. 6, 2020, which is a national stage entry of International Application No. PCT/EP2019/058855, filed on Apr. 8, 2019, which claims the benefit of U.S. Provisional Patent Application No. 62/654,215, filed Apr. 6, 2018 and U.S. Provisional Patent Application No. 62/786,047, filed Dec. 28, 2018. The contents of all of the applications listed above are hereby incorporated by reference as if fully set forth.

TECHNICAL FIELD

The subject matter described herein relates to modular patient monitoring medical devices; and a connector that is able to electrically connect any two or more devices and provides an electrical connection that can be simply physically or tactually confirmed.

BACKGROUND

Monitors that include electronic visual displays are utilized in a large number of applications within a wide variety of industries including, for example, the healthcare industry, the military, and the oil and gas industry. Many of the applications within such industries require such monitors to, at times, be portable, and, at other times, be stationary. For example, in the healthcare industry, when not being used in transport of a patient or when a patient is ambulatory, monitors can be connected to a monitor mount. Such monitor mounts can provide a variety of functions including providing physical support, a power source, and a conduit to one or more computer networks.

One type of monitor is a patient monitor which is used by healthcare facilities to monitor and display information about a patient, such as vital signs, status of connected devices (e.g., physiological sensors, etc.), and the like. Patient monitors can be portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed at the treatment location. Patient monitor mounts can also provide electrical connection to other devices or infrastructure, such as power to recharge patient monitor batteries, network connectivity to other medical devices or hospital computer systems, and the like.

Patient monitors can rely on the acquisition of physiological signals obtained from front-end analog circuits connected to a patient. Patient monitors can process and/or display analog data derived from the patient. Both patient monitors and patient monitor mounts can include various software applications to process and/or transmit data between each other. Software capabilities for such monitors and mounts are continuously evolving. Compatibility between patient monitors and patient monitor mounts can impact monitoring of the patient.

During the course of providing healthcare to patients, practitioners typically connect at least one type of sensor to a patient to sense, derive or otherwise monitor at least one type of patient medical parameter. Such patient connected sensors are further connected to a monitor that includes all relevant electronic components that enable conversion, manipulation and processing of the data sensed by the at least one type of sensor in order to generate patient medical parameters. These patient medical parameters may be stored in one or more modules and are usable by healthcare practitioners (e.g., nurses, doctors, physician assistants, or any other person charged with providing a healthcare service to a patient) in monitoring a patient and determining a course of healthcare to be provided to the patient. Additionally or alternatively, the one or more modules may contain data, such as patient treatment data, to be transferred to the monitor and/or a dock.

Connectors are used to electrically connect at least one or more devices, such as, for example, a patient connected sensor and a module. Conventional connectors often have inconspicuous keying and are difficult to mate with corresponding interfaces, particularly in low light or dark conditions. Such conventional connectors require painstaking visual confirmation of the orientations of the interfaces in order to ensure a proper connection. Therefore, a need exists to provide a connector that has conspicuous keying and external shapes that are asymmetrical and can be felt in low light conditions, are easy to mate with corresponding interfaces, and provide electrical and mechanical connections that can be simply physically or tactually confirmed.

SUMMARY

Systems, methods, and devices are described herein for a modular patient monitoring medical device and a connector. A new generation of physiological measurement devices, such as Intelligent Patient Front End Devices (IPFE) can provide updated algorithms, features, and software updates for parameter measurement devices without corresponding releases of a new version of host monitor software. IPFEs, together with patient sensors, comprise a complete physiological patient parameter measurement delivery system. A number and a type of parameter measurement devices can be configured to meet varied and changing clinical needs. Remote access to versions, logs, self-tests, settings, history, and/or measurements via the Internet to one or more parameter measurement devices can provide a unified service approach.

A system may comprise a monitor mount, a rack, a module, a module connector cable and/or a connector including a male connector and/or a female connector.

In some variations, the module may be configured to be electrically connected to the monitor mount by the module connector cable, the module may be configured to be detachably secured to the rack, the module may include a male connector and one of the rack and the module connector cable may include a female connector. In other variations, a connector may comprise the male connector and the female connector.

The female connector may include a housing including a pair of longitudinal sides, a planar side connecting first ends of the pair of longitudinal sides of the female connector, a rounded side connecting second ends of the pair of longitudinal sides of the female connector, and a front surface including a plurality of sockets located therein, the plurality of sockets being arranged along a line parallel to the pair of longitudinal sides of the female connector.

The male connector may include a housing including a recess with a pair of longitudinal sides, a planar side connecting first ends of the pair of longitudinal sides of the male connector, a rounded side connecting second ends of the pair of longitudinal sides of the male connector, and a recessed surface including a plurality of pins extending therefrom, the plurality of pins being arranged along a line parallel to the pair of longitudinal sides of the male connector.

The housing of the female connector may be configured to be insertable into the recess of the housing of the male connector such that the plurality of pins of the male connector enter into the plurality of sockets of the female connector.

In other variations, the module may be configured to be electrically connected to the monitor mount by the module connector cable, the module may be configured to be detachably secured to the rack, the monitor mount may include a female connector, and the module connector cable may include a male connector.

The female connector may include a housing including a pair of longitudinal sides including ribs formed thereon, a planar side connecting first ends of the pair of longitudinal sides of the female connector, a rounded side connecting second ends of the pair of longitudinal sides of the female connector, and a front surface including a plurality of sockets located therein, the plurality of sockets being arranged along a line parallel to the pair of longitudinal sides of the female connector.

The male connector may include a housing including a recess with a pair of longitudinal sides, a planar side connecting first ends of the pair of longitudinal sides of the male connector, a rounded side connecting second ends of the pair of longitudinal sides of the male connector, and a recessed surface including a plurality of pins extending therefrom, the plurality of pins being arranged along a line parallel to the pair of longitudinal sides of the male connector.

The housing of the female connector may be configured to be insertable into the recess of the housing of the male connector such that the plurality of pins of the male connector enter into the plurality of sockets of the female connector.

A connector may comprise a female connector and a male connector.

The female connector may include a housing including a pair of longitudinal sides, a planar side connecting first ends of the pair of longitudinal sides of the female connector, a rounded side connecting second ends of the pair of longitudinal sides of the female connector, and a front surface including a plurality of sockets located therein, the plurality of sockets being arranged along a line parallel to the pair of longitudinal sides of the female connector.

The male connector may include a housing including a recess with a pair of longitudinal sides, a planar side connecting first ends of the pair of longitudinal sides of the male connector, a rounded side connecting second ends of the pair of longitudinal sides of the male connector, and a recessed surface including a plurality of pins extending therefrom, the plurality of pins being arranged along a line parallel to the pair of longitudinal sides of the male connector.

The housing of the female connector may be configured to be insertable into the recess of the housing of the male connector such that the plurality of pins of the male connector enter into the plurality of sockets of the female connector.

A male connector may comprise a housing including a recess with a pair of longitudinal sides, a planar side connecting first ends of the pair of longitudinal sides, a rounded side connecting second ends of the pair of longitudinal sides, and a recessed surface including a plurality of pins extending therefrom. The pins may be arranged along a line parallel to the pair of longitudinal sides.

A female connector may comprise a housing including a pair of longitudinal sides, a planar side connecting first ends of the pair of longitudinal sides, a rounded side connecting second ends of the pair of longitudinal sides; and a front surface including a plurality of sockets located therein. The sockets may be arranged along a line parallel to the pair of longitudinal sides.

The pair of longitudinal sides of the male connector or the pair of longitudinal sides of the female connector may include ribs formed thereon.

The male connector or the female connector may include at least one shield spring formed therein. The at least one shield spring may be formed in one of the longitudinal sides, the rounded side, and/or the planar side.

The male connector or the female connector may include at least one shield protrusion formed thereon. The at least one shield protrusion may be formed on one of the longitudinal sides, the rounded side, and/or the planar side.

The male connector or the female connector may include at least one shield groove formed therein. The at least one shield groove may be formed in one of the longitudinal sides, the rounded side, and/or the planar side.

A shroud may be included at the planar side of the male connector or the planar side of the female connector.

A gasket may surround the housing of the male connector or the housing of the female connector.

The housing of the female connector may be configured to be insertable into the recess of the housing of the male connector such that at least one shield protrusion of the male connector compresses at least one shield spring of the female connector.

An external shape of one of the male connector and the female connector may be asymmetrical such that the one of the male connector and the female connector may be configured to be connected to the other of the male connector and the female connector in only one orientation.

As discussed above, the female connector may include a plurality of sockets. In one particular embodiment, the female connector comprises any one or more of the following number of sockets: 1, 2, 3, 4, 5, 6, 7, 8, 9, 10, 11, 12, 13, 14, 15, 16, 17, 18, 19, or 20. In a preferred embodiment, the female connector comprises 7 sockets.

As discussed above, the male connector may include a plurality of pins. In one particular embodiment, the male connector comprises any one or more of the following number of pins: 1, 2, 3, 4, 5, 6, 7, 8, 9, 10, 11, 12, 13, 14, 15, 16, 17, 18, 19, or 20. In a preferred embodiment, the male connector comprises 7 pins.

The male connector or the female connector may include a shield configured to contact the at least one shield spring. The shield may be a 360° shield.

The male connector or the female connector may include at least one of a contact holder, a socket holder, or shield tabs.

The male connector or the female connector may include holes for receiving fasteners.

A cable may join the male connector and the female connector.

The system may further comprise a cable and a circular connector, the cable joining the male connector or the female connector and the circular connector.

The connector may be configured to be electrically connected to a monitor mount and/or a rack.

The male connector and the female connector may be configured to be connected through a back wall of a rack.

The male connector or the female connector may be defined in a rack, a monitor mount, a module, and/or at an end of a cable.

The monitor mount may be configured to detachably secure a patient monitor configured to monitor and display information about a patient.

The module may be a patient monitoring module configured to acquire and process data generated by at least one physiological sensor configured to monitor a physiological parameter of a patient.

Non-transitory computer program products (i.e., physically embodied computer program products) are also described that store instructions, which when executed by one or more data processors of one or more computing systems, cause at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including, but not limited to, a connection over a network (e.g., the Internet, a wireless wide area network, a local area network, a wide area network, a wired network, or the like), via a direct connection between one or more of the multiple computing systems, etc.

The subject matter described herein provides many technical advantages. For example, the current subject matter as described herein provides plug-and-play capabilities for patient monitors and/or one or more physiological parameter measurement pods. Use of the subject matter described herein can improve software integration capabilities of consuming medical devices, such as physiological parameter measurement pods, with patient monitors. Such integration capabilities can additionally provide for decoupled software development of one or more physiological parameter measurement pods and one or more patient monitors. The connector has conspicuous keying and external shapes that are asymmetrical and can be felt in low light conditions, are easy to mate with corresponding interfaces, and provide electrical and mechanical connections that can be simply physically or tactually confirmed.

The details of one or more variations of the subject matter described herein are set forth in the accompanying drawings and the description below. Other features and advantages of the subject matter described herein will be apparent from the description and drawings, and from the claims.

DETAILED DESCRIPTION

Physiological parameter measurement pods are devices for measuring one or more patient physiological parameters of a patient. Such data acquisition devices can self-describe the data produced and adjust configuration settings based on a particular connection environment. Self-describing physiological parameter measurement pods can allow medical devices to use data with minimal to no software updates. The present subject matter is described in detail herein.

Figures 1A, 1B:
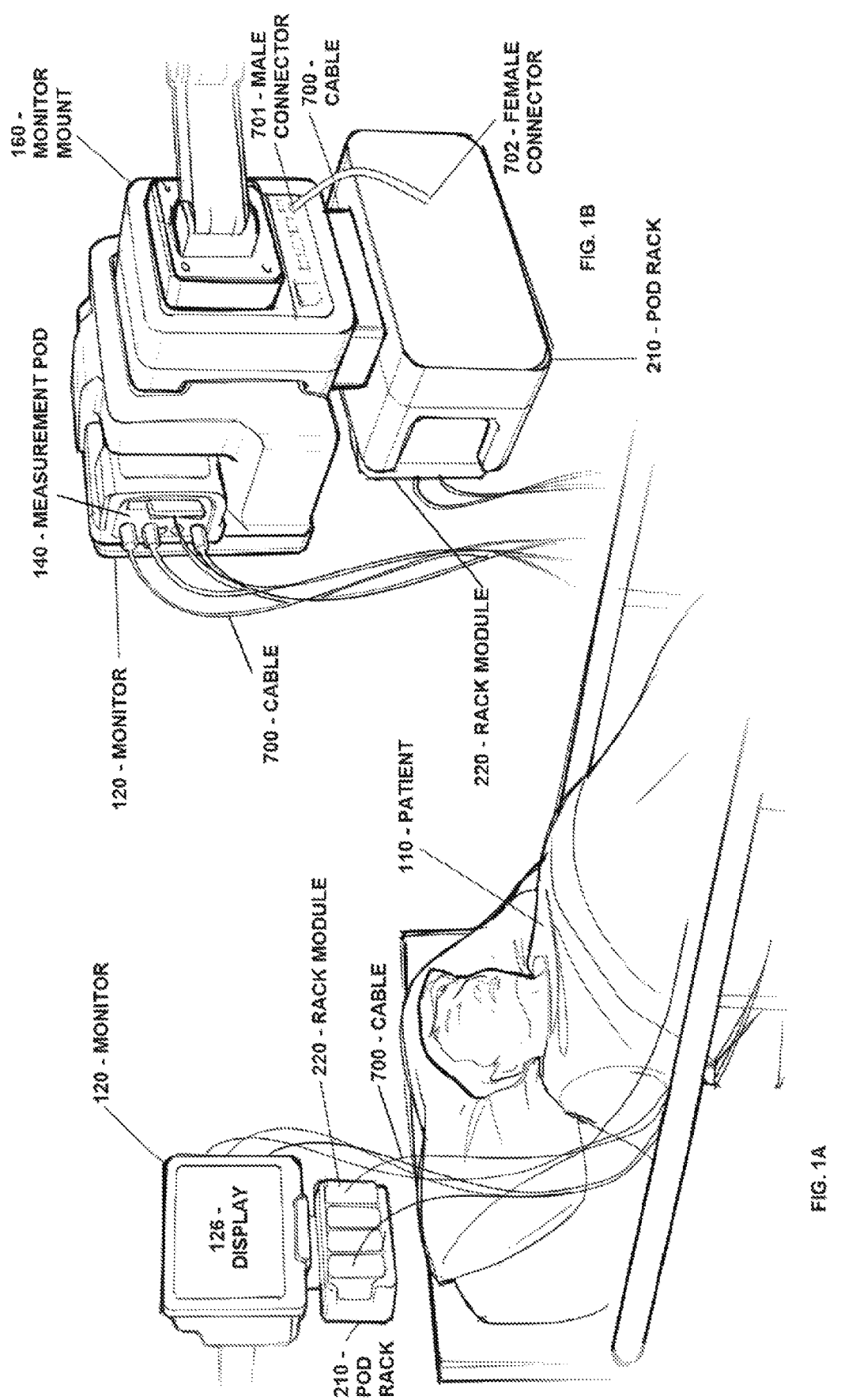
FIGS. 1A and 1B are front and rear perspective views of an example environment for an example system including a monitor 120, a physiological parameter measurement pod 140, a monitor mount 160, a physiological parameter measurement pod rack 210, a rack module 220, one or more cables 700, a male connector 701, and a female connector 702.

FIGS. 1A and 1B are front and rear perspective views of an example environment for an example system including a monitor 120, a physiological parameter measurement pod 140, a monitor mount 160, a physiological parameter measurement pod rack 210, one or more rack modules 220, at least one cable 700, a male connector 701, and a female connector 702. In the embodiment shown in FIGS. 1A and 1B, at least one cable 700 including a male connector 701 and a female connector 702 may be used to electrically connect the monitor mount 160, the physiological parameter measurement pod rack 210, and/or the one or more rack modules 220.

Figure 2:
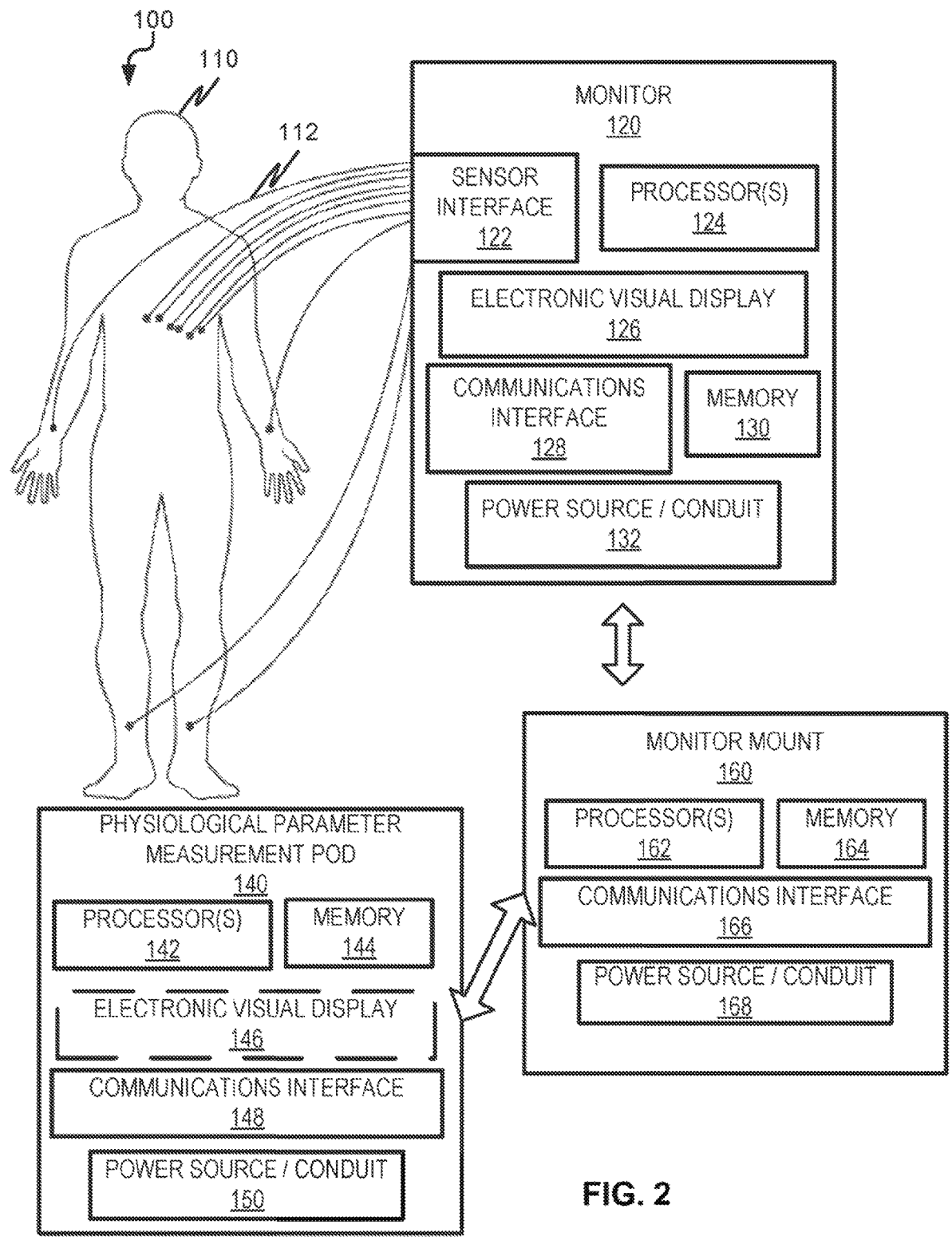
FIG. 2 is a logic diagram illustrating a monitor 120, a physiological parameter measurement pod 140, and a monitor mount 160 and the various components identified therein.

FIG. 2 is a logical diagram 100 of a monitor 120, a physiological parameter measurement pod 140, and a monitor mount 160 which can detachably secure (or otherwise physically interface) with both of the monitor 120 and the physiological parameter measurement pod 140. As will be described in further detail below, the monitor 120 can have a shape and size which differs from that of the physiological parameter measurement pod 140. Nonetheless, both of the monitor 120 and the physiological parameter measurement pod 140 are able to be concurrently secured to the monitor mount 160. In addition, while certain configurations are illustrated in FIG. 2 with regard to the monitor mount 160, the monitor 120, and the physiological parameter measurement pod 140, it will be appreciated that these illustrations are examples and not limiting in nature (unless otherwise specified).

The monitor 120 can, for example, be a patient monitor that is used to monitor various physiological parameters for a patient 110. With such a variation, the monitor 120 can include a sensor interface 122 that can be used to connect via wired and/or wireless interfaces to one or more physiological sensors and/or medical devices 112 (e.g., ECG electrodes, SPO2 sensors, blood pressure cuffs, apnea detection sensors, respirators, etc.) associated with the patient 110. The monitor 120 can include one or more processors 124 (e.g., programmable data processors, etc.) which can execute various instructions stored in memory 130 of the monitor 120. Various data and graphical user interfaces can be conveyed to a user via an electronic visual display 126. This information can, for example, relate to the measured physiological parameters of the patient 110 and the like (e.g., blood pressure, heart related information, pulse oximetry, respiration information, etc.). Other types of information can also be conveyed by the electronic visual display 126. In some variations, the electronic visual display 126 includes a touch screen interface.

The monitor 120 can additionally include a communications interface 128 which allows the monitor 120 directly or indirectly (via, for example, the monitor mount 160) to access one or more computing networks. The communications interface 128 can include various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the monitor 120.

The monitor 120 can optionally also include a power source and/or conduit 132 that can be used to power the various components of the monitor 120. The power source/conduit 132 can include a self-contained power source such as a battery pack and/or the power source/conduit 132 can include an interface to be powered through an electrical outlet (either directly or by way of the monitor mount 160).

Physiological parameter measurement pods 140 are devices for measuring one or more patient physiological parameters of the patient 110. Additionally, physiological parameter measurement pods 140 can facilitate the exchange of data related to the physiological parameters of the patient 110 with a patient monitoring device, such as the monitor 120. The physiological parameter measurement pod 140 can include one or more processors 142 (e.g., programmable data processors, etc.) which can execute various instructions stored in memory 144 of the physiological parameter measurement pod 140. In some variations, various data and graphical user interfaces can be conveyed to a user via an electronic visual display 146. This information can, for example, relate to the measured physiological parameters of the patient 110 and the like (e.g., blood pressure, heart related information, pulse oximetry, respiration information, etc.) as received from the monitor 120. Other types of information can also be conveyed by the electronic visual display 146. In some variations, the electronic visual display 146 includes a touch screen interface.

The physiological parameter measurement pod 140 can additionally include a communications interface 148 which allows the physiological parameter measurement pod 140 directly or indirectly (via, for example, the monitor 120 and/or the monitor mount 160) to access one or more computing networks. The communications interface 148 can include various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the physiological parameter measurement pod 140 and from the monitor 120 to the physiological parameter measurement pod 140.

The physiological parameter measurement pod 140 can optionally also include a power source and/or conduit 150 that can be used to power the various components of the monitor 120. The power source/conduit 150 can include a self-contained power source such as a battery pack and/or the power source/conduit 150 can include an interface to be powered through an electrical outlet (either directly or by way of the monitor 120 and/or the monitor mount 160). In some variations, the physiological parameter measurement pod 140 can only be powered and render information when secured or otherwise connected to one or more of the monitor 120 and the monitor mount 160.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 directly or indirectly to access one or more computing networks. The communications interface 166 can include various network cards/interfaces to enable wired and wireless communications with such computing networks. The communications interface 166 can also enable direct (i.e., device-to-device, etc.) communications (i.e., messaging, signal exchange, etc.) such as with the monitor 120 and/or the physiological parameter measurement pod 140.

The monitor mount 160 can optionally also include a power source and/or conduit 168 that can be used to power the various components of the monitor mount 160 and/or the monitor 120 and the physiological parameter measurement pod 140 when secured to the monitor mount 160. The power source/conduit 168 can include a self-contained power source such as a battery pack and/or the power source/conduit 168 can include an interface to be powered through an electrical outlet.

In some variations, the one or more processors 162 and the memory 164 are omitted such that the monitor mount 160 provides only physical support and optionally a power source.

The monitor mount 160 has a shape and size which allows the monitor mount 160 to detachably secure both the monitor 120 and the physiological parameter measurement pod 140. In this regard, "detachably secure" means that the monitor mount 160 can secure the monitor 120 and the physiological parameter measurement pod 140 such that the monitor 120 and/or the physiological parameter measurement pod 140 can be removed by a user when desired.

The positioning of the monitor 120, when secured to the monitor mount 160, can be such that the communications interface 128 on the monitor 120 interacts with the communications interface 166 of the monitor mount 160 to allow, for example, a direct connection (e.g., electrical connection). In other variations, the communications interface 128 of the monitor 120 exchanges data with the communications interface 166 of the monitor mount 160 optically (via, for example, respective optical windows on the monitor 120 and the monitor mount 160).

The positioning of the monitor 120 when secured to the monitor mount 160 can also align the power source/conduit 132 of the monitor 120 to be coupled to the power source/conduit 168 of the monitor mount 160 which causes the monitor mount 160 to power the monitor 120.

Any of the monitor mount 160, the monitor 120, and the physiological parameter measurement pod 140 can optionally also include an interface configured to receive a connector 701-702"" of a cable 700-700" or wired connection for connecting a module, a monitor, device, other external unit or the like.

Figure 3:
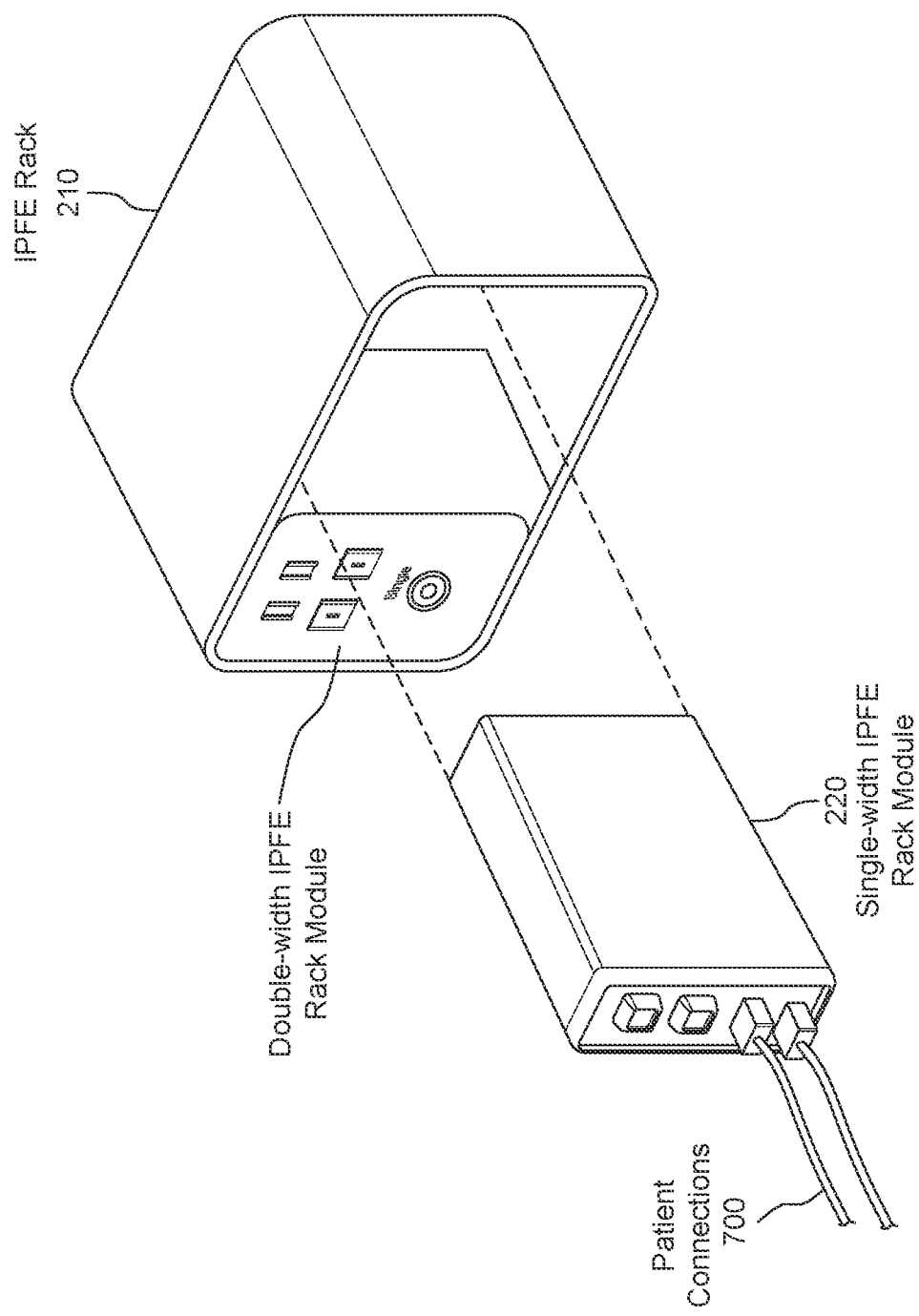
FIG. 3 is an example physiological parameter measurement pod rack 210 having a rack slot to accommodate a rack module 220 with at least one example patient connection 700 extending therefrom.

FIG. 3 is an example physiological parameter measurement pod rack 210 having a rack slot for a rack module 220. In some variations, the rack module 220 can be detachably secured within one or more slots of the physiological parameter measurement pod rack 210. One or more cables 700-700", i.e., patient connections as shown in the embodiment in FIG. 3, can be coupled to the rack module 220 for transmission of one or more physiological patient parameters of the patient 110. In other variations, the physiological patient parameter pod rack 210 can be a modular pod rack as described by WO 2015/094248 titled "Rack Mounted Modules," the entire contents of which are hereby fully incorporated by reference. An example of physiological patient parameter pods 140 for use in connection with subject matter described herein can include those described in U.S. Pat. No. 6,221,012 B1, titled "Transportable Modular Patient Monitor with Data Acquisition Modules," the entire contents of which are hereby fully incorporated by reference.

The rack module 220 can provide one or more different functions used in delivering healthcare to a patient. The rack module 220 can acquire patient data including the monitored parameters allocated to a given patient from a network and collate the information for storage in a database. The rack module 220 can be any of a patient monitoring module for acquiring and processing data generated by at least one physiological sensor monitoring a physiological parameter of a patient (e.g., gas measurement, end-tidal carbon dioxide (etCO2), SCIO, patient gas, thermoregulation, blood pressure, heart related measurement, pulse oximetry, respiration, neonatal measurement, ventilation, anesthesia information, incubation information, etc.), a patient treatment module for delivering treatment to the patient (e.g., supplying fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, a Trace Work Area (TWA) control module, an output board, a dock module, an adapter module, a passive treatment module, an active treatment module, etc. A processor can process signals derived from the rack module 220.

Figure 4:
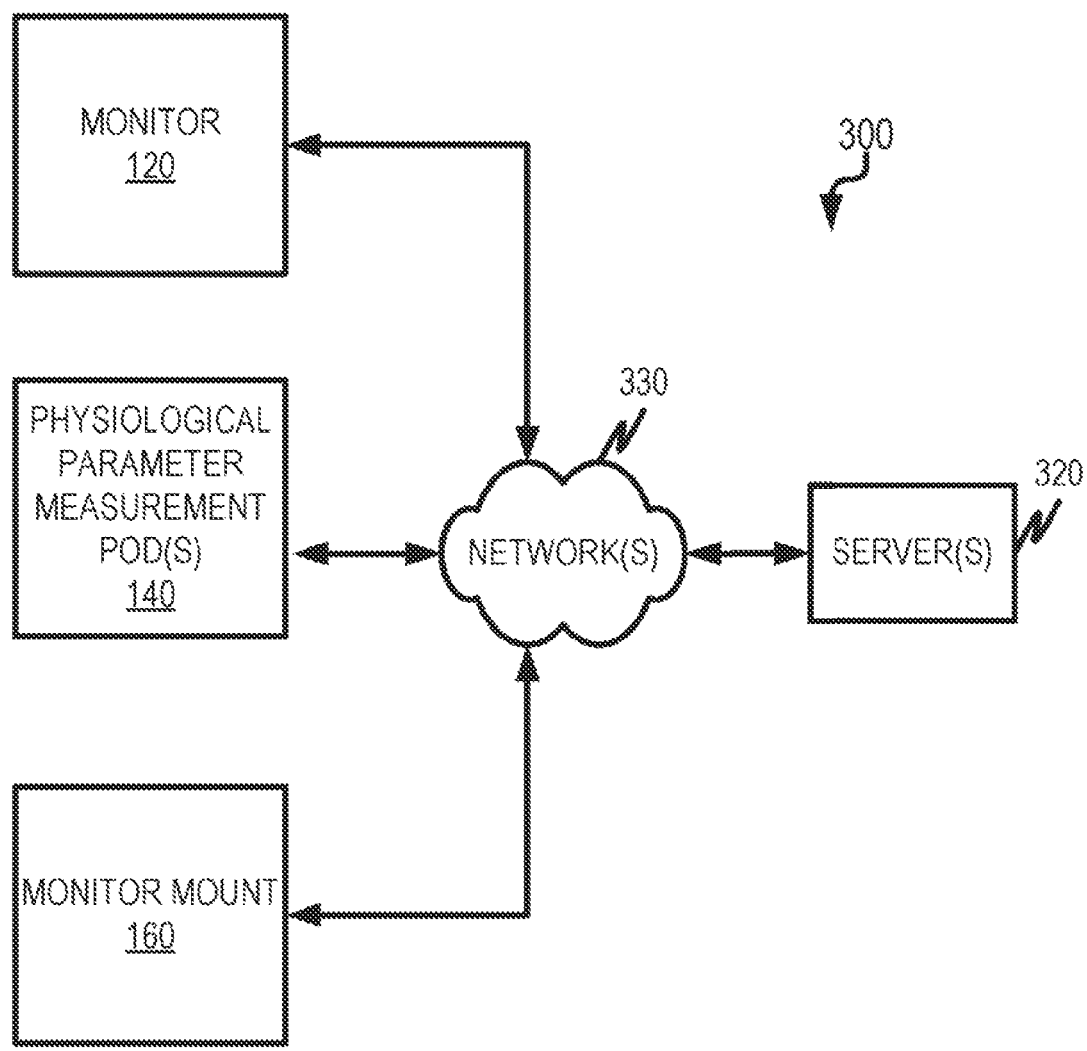
FIG. 4 is a system block diagram illustrating an architecture 300 for use in connection with the current subject matter.

FIG. 4 is a system block diagram illustrating an architecture 300 for use in connection with the current subject matter. The current subject matter is described in connection with an arrangement involving the monitor 120, the one or more physiological parameter measurement pods 140, the monitor mount 160, and one or more servers 320 which can communicate over one or more networks 330. Each of the monitor 120, the one or more physiological parameter measurement pods 140, the monitor mount 160, and the one or more servers 320 can comprise one or more programmable data processors and memory for storing instructions for execution by such programmable data processor(s). Furthermore, it will be appreciated that each of the monitor 120, the one or more physiological parameter measurement pods 140, the monitor mount 160, and the one or more servers 320 can comprise more than one computing device depending on the desired configuration and that the illustration in FIG. 4 is simplified to aid in the understanding of the current subject matter. Software configurations and/or updates to the monitor 120, the one or more physiological parameter measurement pods 140, and/or the monitor mount 160 can be transmitted via the network(s) 330. The network(s) 330 can be wireless network(s) and/or wired network(s).

Figure 5:
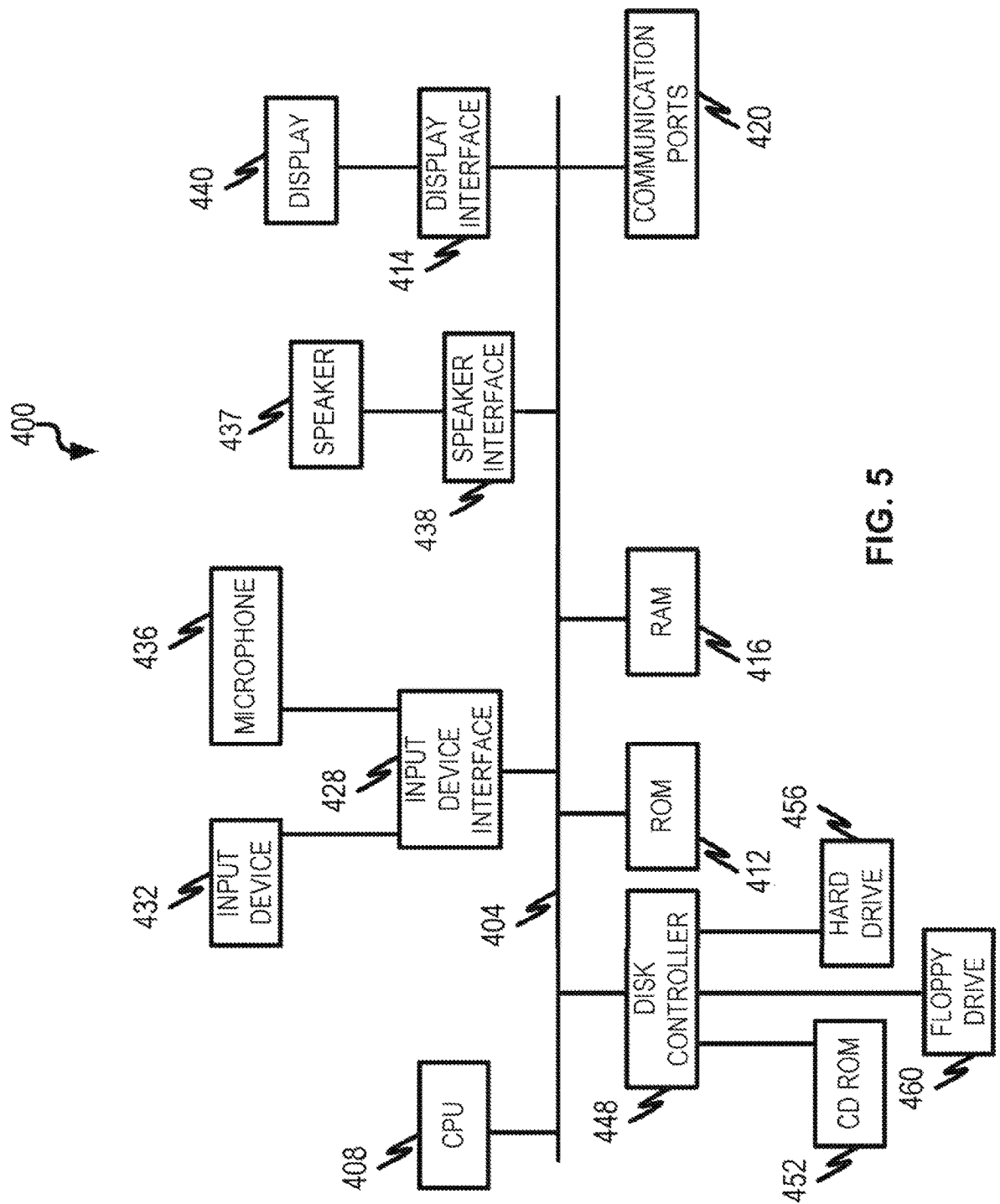
FIG. 5 is a diagram illustrating a sample computing device architecture 400 for implementing various aspects described herein.

FIG. 5 is a diagram illustrating a sample computing device architecture 400 for implementing various aspects described herein. A system bus 404 can serve as the information highway interconnecting the other illustrated components of the hardware. A processing system 408 labeled CPU (central processing unit) (e.g., one or more computer processors/data processors at a given computer or at multiple computers) can perform calculations and logic operations required to execute a program. A non-transitory processor-readable storage medium, such as read only memory (ROM) 412 and random access memory (RAM) 416, can be in communication with the processing system 408 and can include one or more programming instructions for the operations specified here. Optionally, program instructions can be stored on a non-transitory computer-readable storage medium such as a magnetic disk, an optical disk, a recordable memory device, flash memory, or another physical storage medium.

In one example, a disk controller 448 can act as an interface between one or more optional disk drives and the system bus 404. These disk drives can be external or internal floppy disk drives such as 460, external or internal CD-ROM, CD-R, CD-RW or DVD, or solid state drives such as 452, or external or internal hard drives 456. As indicated previously, these various disk drives 452, 456, 460 and disk controllers are optional devices. The system bus 404 can also include at least one communication port 420 to allow for communication with external devices either physically connected to the computing system or available externally through a wired or wireless network. In some cases, the communication port 420 includes or otherwise comprises a network interface.

To provide for interaction with a user, the subject matter described herein can be implemented on a computing device having a display 440 (e.g., a CRT (cathode ray tube) or LCD (liquid crystal display) monitor) for displaying information obtained from the system bus 404 to the user and an input device 432 such as a keyboard and/or a pointing device (e.g., a mouse or a trackball) and/or a touchscreen by which the user can provide input to the computer. Other kinds of input devices 432 can be used to provide for interaction with a user as well. For example, feedback provided to the user can be any form of sensory feedback (e.g., visual feedback, auditory feedback by way of a speaker 437, or tactile feedback), and input from the user can be received in any form, including acoustic, speech, or tactile input. The input device 432 and a microphone 436 can be coupled to and convey information via the system bus 404 by way of an input device interface 428. The speaker 437 can be coupled to and receive information via the system bus 404 by way of a speaker interface 438. Other computing devices, such as dedicated servers, can omit one or more of the display 440, the display interface 414, the input device 432, the microphone 436, the speaker 437, the input device interface 428 and the speaker interface 438.

In the embodiments shown in FIGS. 6-21, male and female connectors 701-702" can be used to electrically connect any two or more devices (e.g., a monitor mount 160, a physiological parameter measurement pod rack 210, a rack module 220, and/or a medical device 112 or sensor connected to a patient 110).

FIGS. 6-21 show various exemplary implementations of cables 700-700", male connectors 701-701", and female connectors 702-702"". The male and female connectors 701-702" can be used to electrically connect any two or more devices (e.g., a monitor mount 160, a physiological parameter measurement pod rack 210, a rack module 220, and/or a medical device or sensor 112 connected to a patient 110). In particular, the male and female connectors 701-702" enable power sharing and/or data transfer between the two or more devices.

Figure 8:
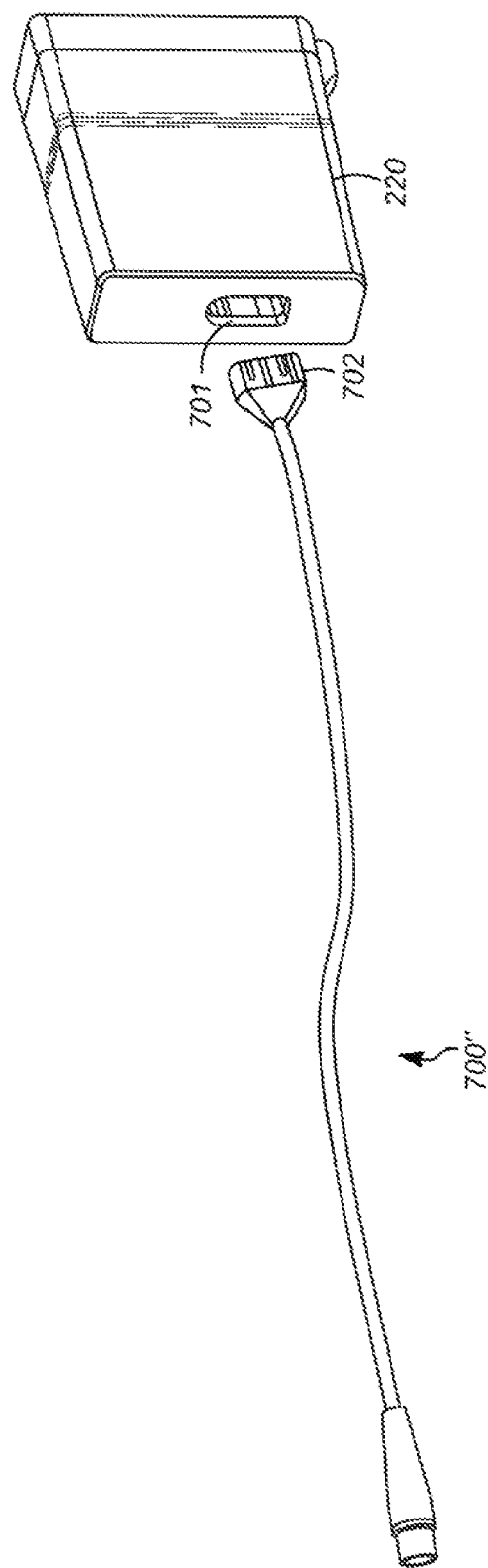
FIG. 8 is an exploded back perspective view of an exemplary system including a rack module 220, and a third exemplary implementation of a cable 700".
Figure 9:
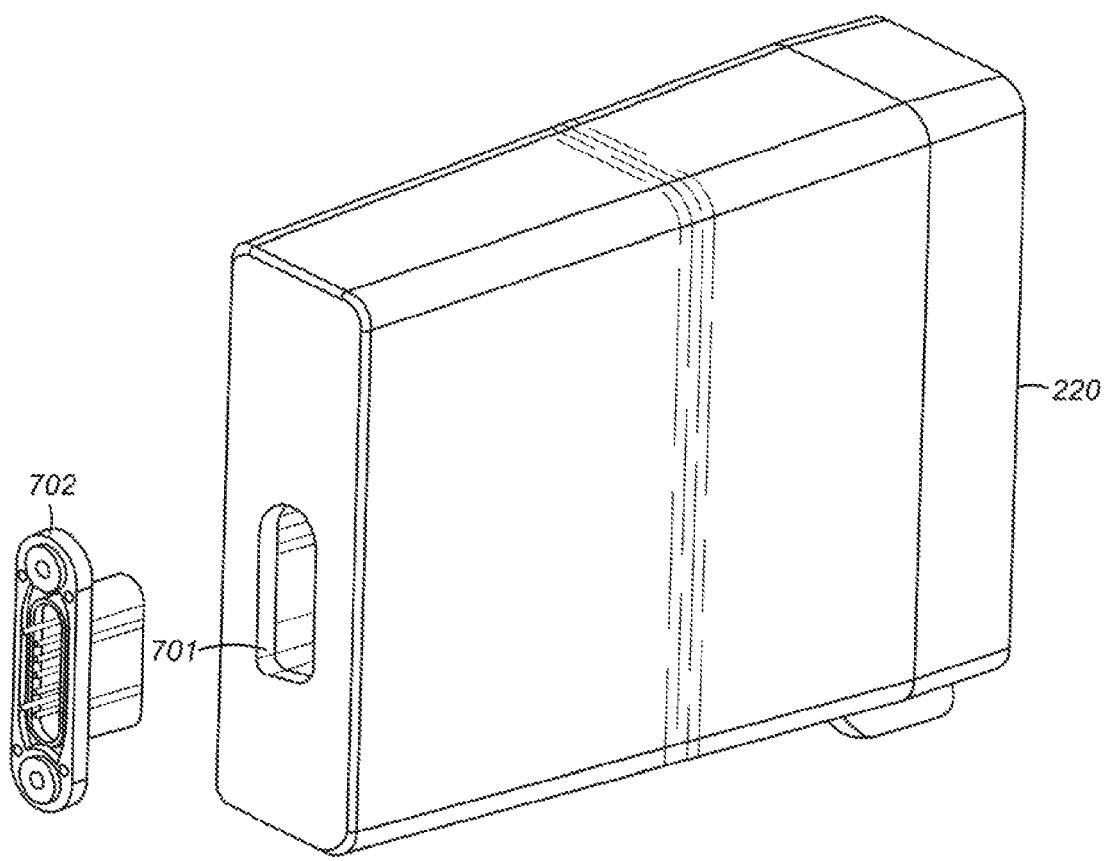
FIG. 9 is an exploded back perspective view of an exemplary system including a rack module 220, a male connector 701 and a female connector 702.

In some variations, the male connectors 701-701" and the female connectors 702-702"" can be configured in any of cable, monitor mount, or rack versions. For example, in the embodiments shown in FIGS. 9, 12, 15 and 16, the male connector 701 of the rack module 220 and the female connector 702 can electrically and mechanically connect directly to each other whereby no cable is integrated with the female connector 702. As shown in FIG. 8, for example, a cable 700' is integrated with the female connector 702'. The cable 700" may function as a connection from the rack module 220 to the monitor mount 160 or a monitor 120 by circumventing the physiological parameter measurement pod rack 210. In other words, the rack module 220 may be directly connected to the monitor mount 160 or the monitor 120 via the cable 700". For example, female connectors 702-702" can be connected to male connectors 701".

As shown in FIGS. 10A-10D, for example, the female connector 702-702"" includes a housing 719 including a pair of longitudinal sides, a planar side connecting first ends of the pair of longitudinal sides of the female connector 702-702"", a rounded side connecting second ends of the pair of longitudinal sides of the female connector 702-702" ", and a front surface including a plurality of sockets 703 located therein, the plurality of sockets 703 being arranged along a line parallel to the pair of longitudinal sides of the female connector 702-702".

Figure 11A:
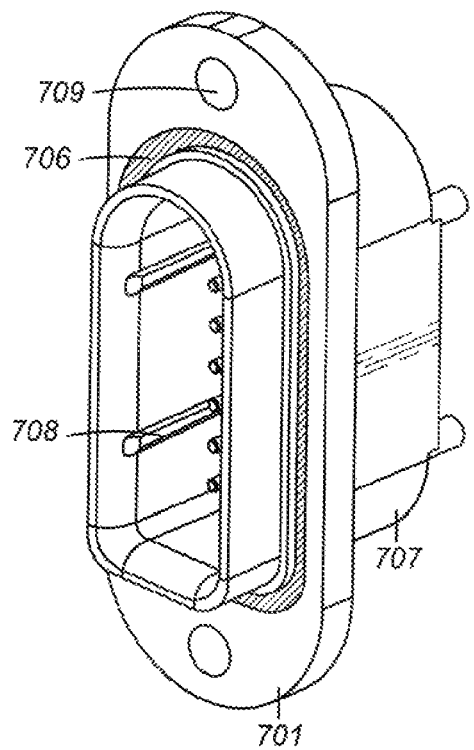
FIGS. 11A and 11B are perspective views of exemplary implementations of the male connector 701 and 701'.
Figure 11B:
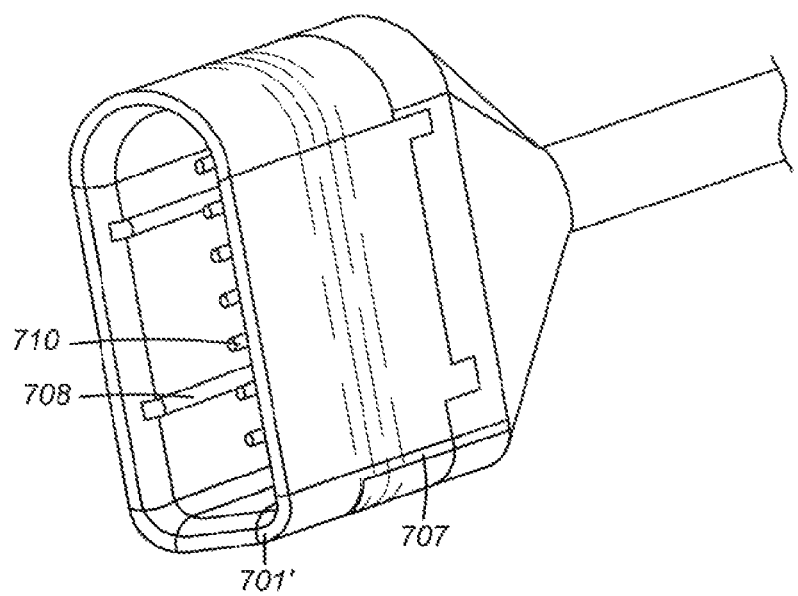
Figure 12:
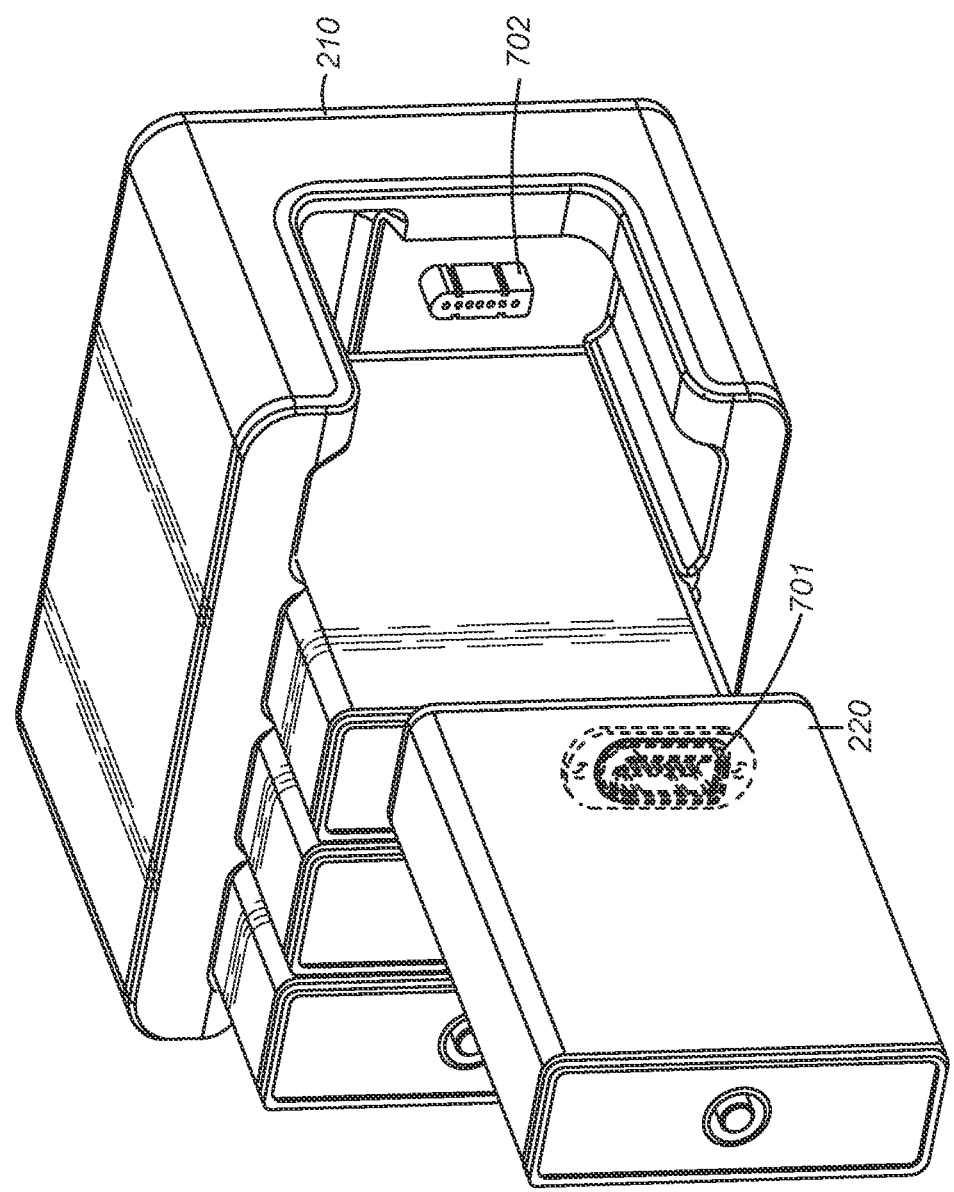
FIG. 12 is an exploded perspective view of an exemplary system including a physiological parameter measurement pod rack 210, and rack modules 220.

As shown in FIGS. 11A and 11B, for example, the male connector 701-701" includes a housing 707 including a recess with a pair of longitudinal sides, a planar side connecting first ends of the pair of longitudinal sides of the male connector 701-701", a rounded side connecting second ends of the pair of longitudinal sides of the male connector 701-701", and a recessed surface including a plurality of pins 710 extending therefrom, the plurality of pins 710 being arranged along a line parallel to the pair of longitudinal sides of the male connector 701-701".

Figure 15:
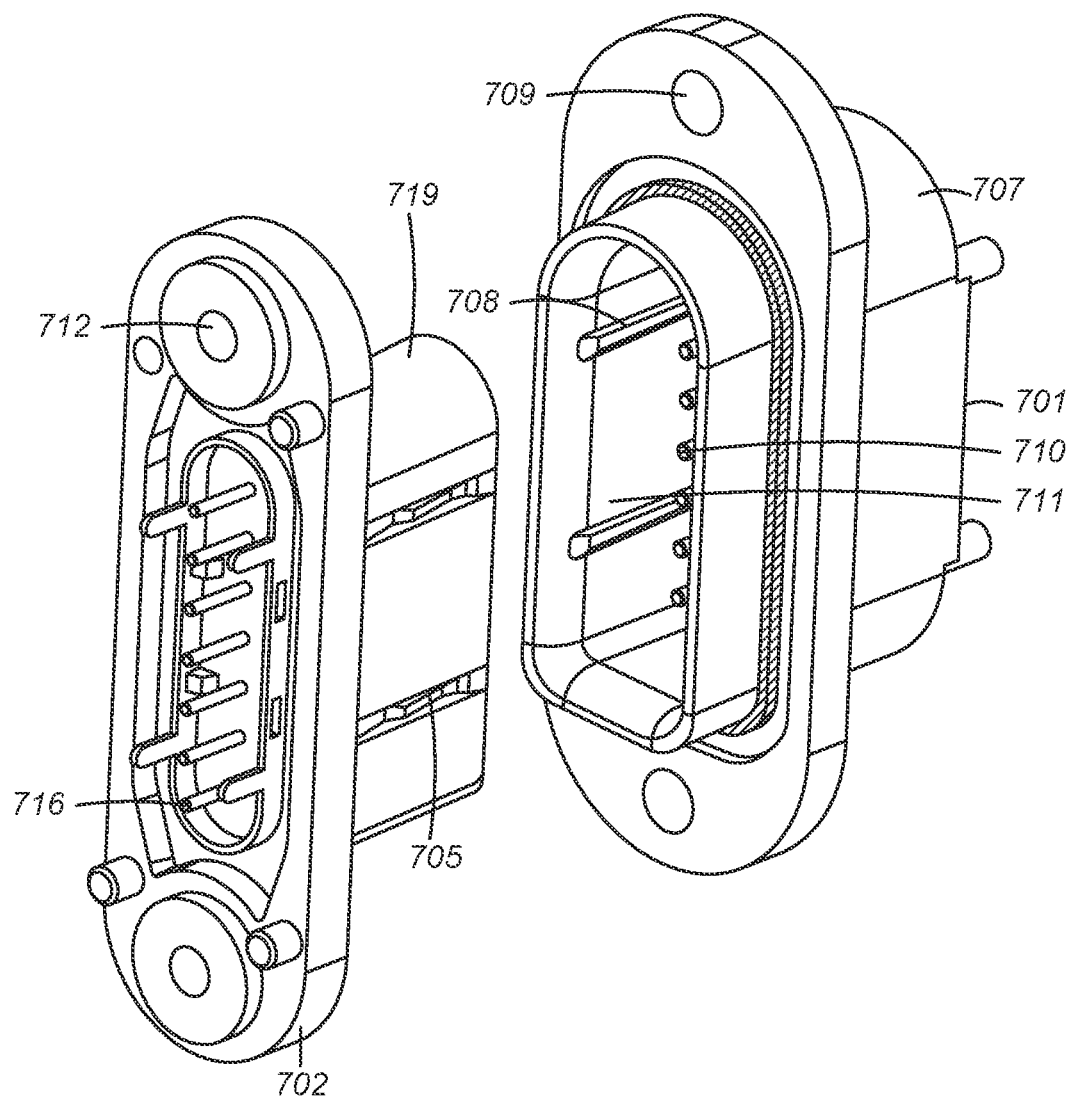
FIG. 15 is an exploded perspective view of the male connector 701 and the female connector 702.
Figure 16:
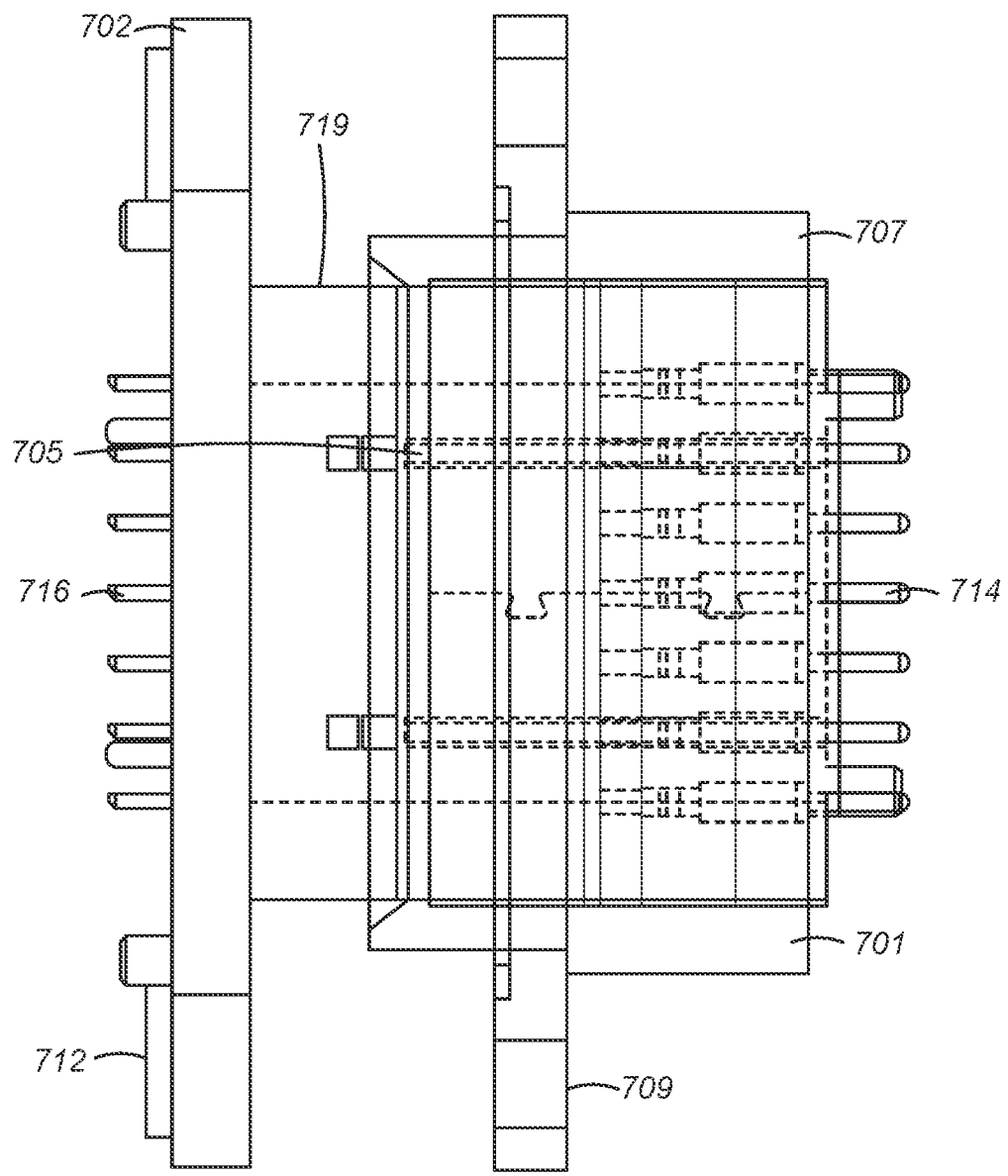
FIG. 16 is a side view of the male connector 701 and the female connector 702.

As shown in FIGS. 15 and 16, for example, the housing 719 of the female connector 702-702"" is configured to be insertable into the recess of the housing 707 of the male connector 701-701" such that the plurality of pins 710 of the male connector 701-701" enter into the plurality of sockets 703 of the female connector 702-702"". In some variations, the male connector 701-701" may include seven pins 710 and the female connector 702-702"" may include seven sockets 703. In the embodiment shown in FIG. 12, the male connector 701-701" and the female connector 702-702" can be connected through a back wall of a physiological parameter measurement pod rack 210.

Figure 10A:
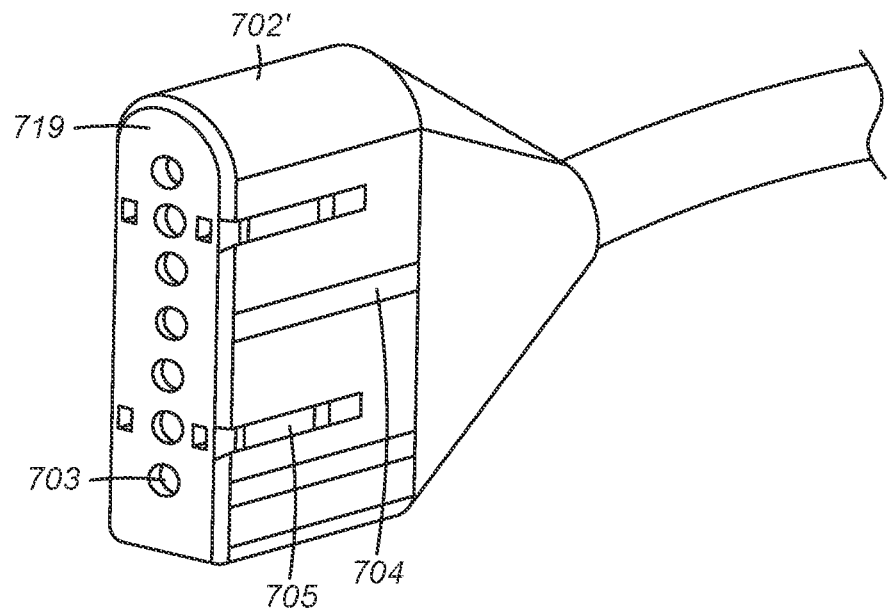
FIGS. 10A-10D are perspective views of exemplary implementations of the female connector 702, 702', 702", and 702'".
Figure 10B:
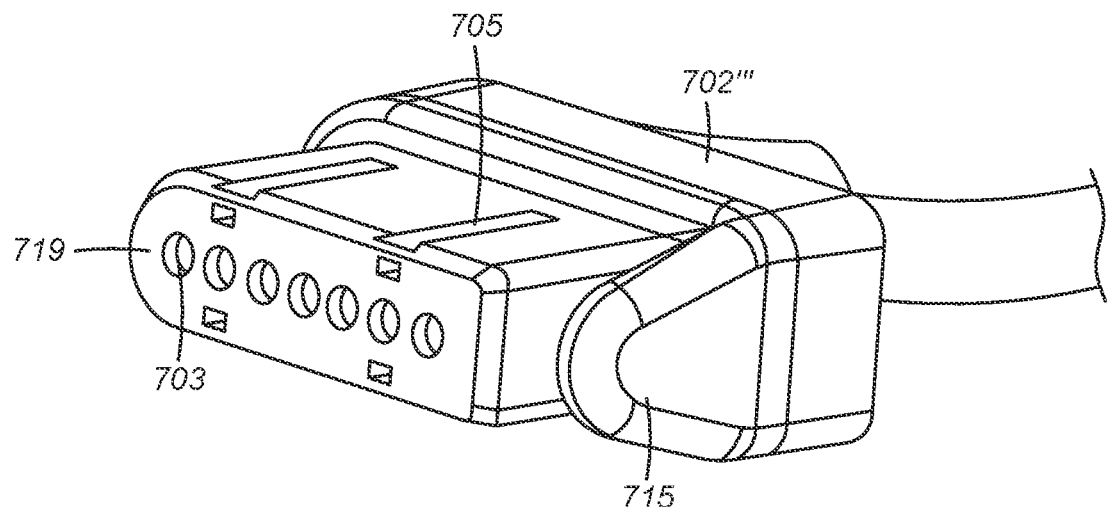
Figure 10C:
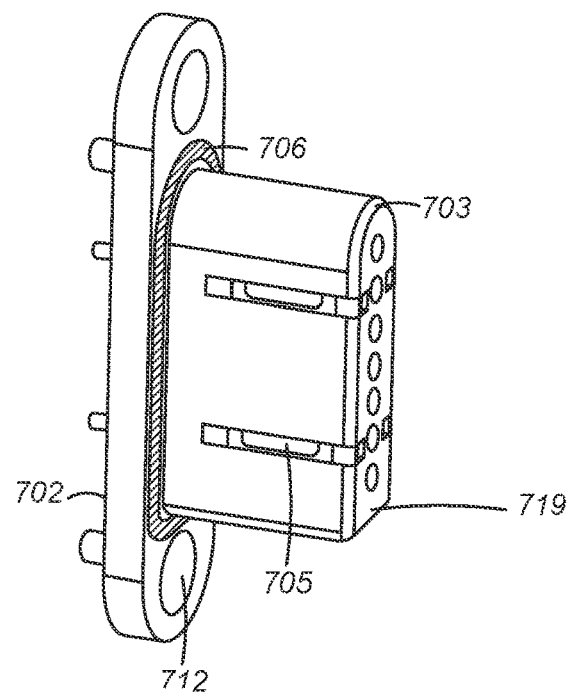
Figure 10D:
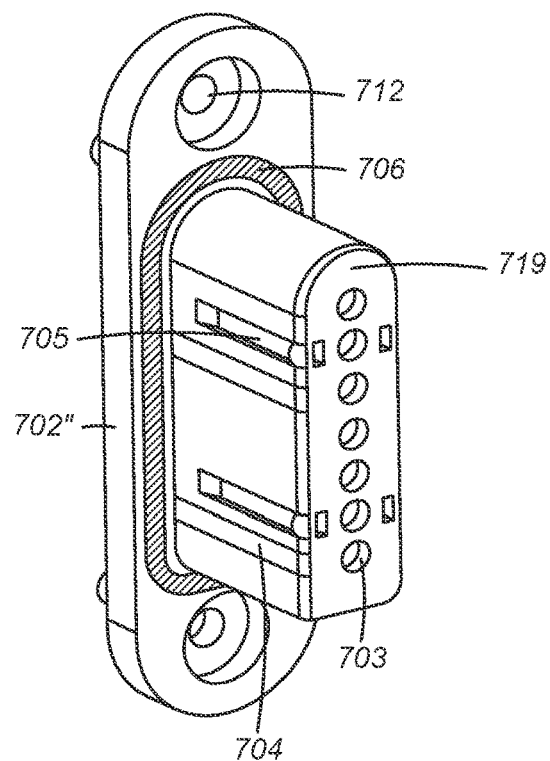

As shown in FIGS. 10A and 10D, for example, the pair of longitudinal sides of the male connector 701-701" or the pair of longitudinal sides of the female connector 702-702"" may include ribs 704 formed thereon. The ribs 704 may increase friction such that the connector having the ribs 704 cannot be inserted into an incorrect device or interface. For example, the monitor mount 160 may include a female connector 702" having ribs 704. The ribs 704 may increase friction such that a sturdier electrical and mechanical connection is provided. The cables 700-700" may also include a female connector 702' having ribs 704.

In some variations, as shown in FIGS. 13B and 17D-18, for example, the male connector 701-701" may include a shield 711 including at least one shield protrusion 708 that provides electromagnetic interference (EMI) protection during signal transfer. As shown in FIGS. 17A-17C, for example, the female connector 702-702"" may include at least one shield spring 705 for receiving the shield protrusions 708. The shield spring 705 can be formed in one of the longitudinal sides, the rounded side, and/or the planar side of the female connector 702-702"". The female connector 702-702"" may also include a shield 718 as shown in FIG. 19. Accordingly, the male connector 701-701" and the female connector 702-702"" are configured to engage with each other sufficiently to ensure that the shield protrusion 708 fully compresses the shield spring 705. The shield 711 may be a 360° shield and an edge of the 360° shield may make contact with the highest point of the shield spring 705.

Alternatively, in embodiments not shown, the male connector 701-701" may include at least one shield spring 705 and the female connector 702-702" may include at least one shield protrusion 708. The shield spring 705 can be formed in one of the longitudinal sides, the rounded side, and/or the planar side of the male connector 701-701".

Figure 6:
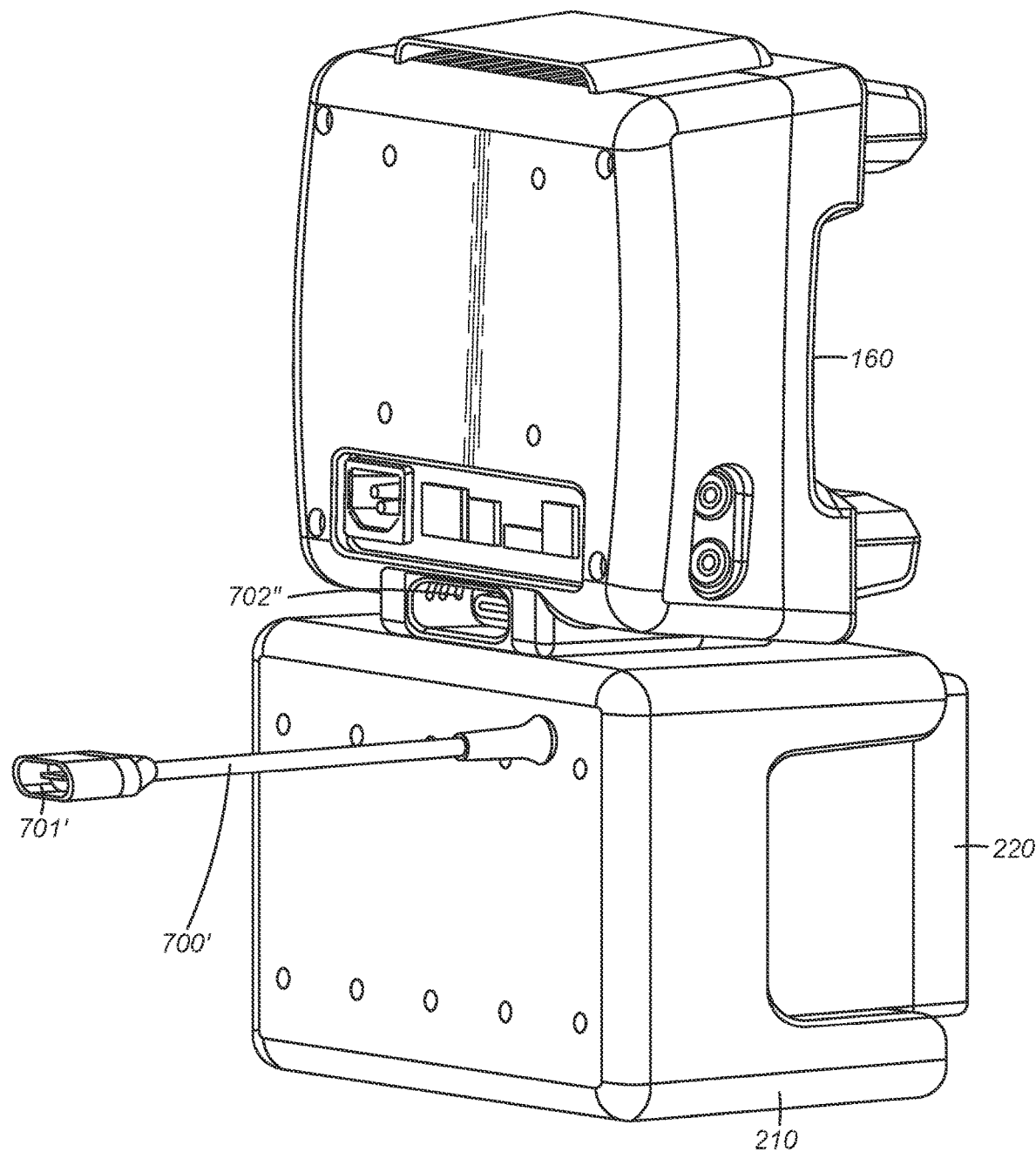
FIG. 6 is a back perspective view of an exemplary system including a monitor mount 160, a physiological parameter measurement pod rack 210, a rack module 220, and a first exemplary implementation of a cable 700.
Figure 7:
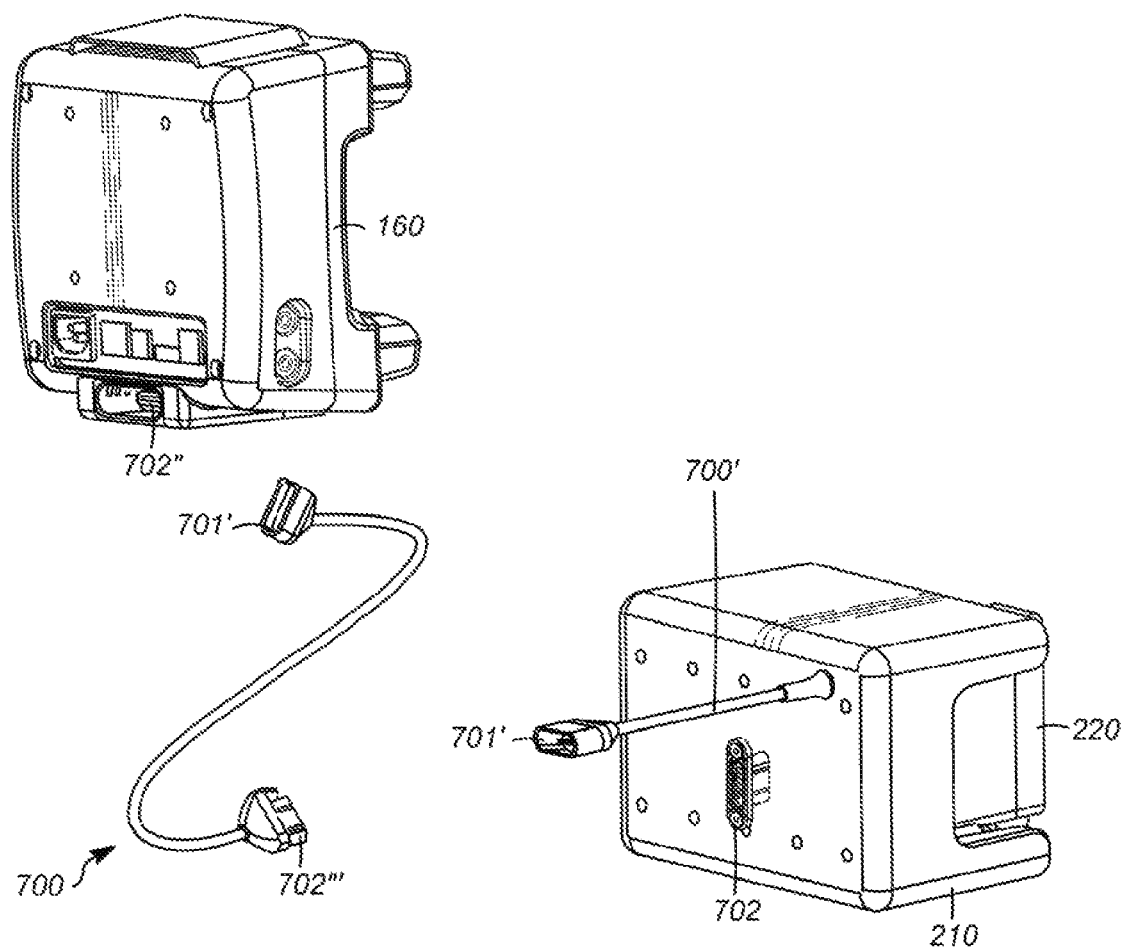
FIG. 7 is an exploded back perspective view of an exemplary system including a monitor mount 160, a physiological parameter measurement pod rack 210, a rack module 220, and first and second exemplary implementations of cables 700 and 700'.

In addition, a minimum engagement required for full shield contact compression may be 4.86 mm. As shown in FIGS. 10C-11A, for example, a gasket 706 may be provided on either of the male connector 701-701" or the female connector 702-702"" to provide sealing. The gasket 706 may surround the housing 707 of the male connector 701-701" or the housing 719 of the female connector 702-702"". The male connector 701-701" may include holes 709 for fasteners. Similarly, the female connector 702-702"" may also include holes 712 for fasteners. One end of any of the cables 700-700" may feature a circular connector for electrical connection with a device, as shown in FIGS. 6-8, for example. A length of any of the cables 700-700" may be less than 3 meters.

As discussed above, an external shape of one of the male connector 701-701" and the female connector 702-702"" is asymmetrical such that the one of the male connector 701-701" and the female connector 702-702"" is configured to be connected to the other of the male connector 701-701" and the female connector 702-702"" in only one orientation.

As shown in FIG. 10B, for example, one of the male connector 701-701" and the female connector 702-702" may include a shroud 715 for ensuring that the connector cannot be inserted into an incorrect device or interface. The shroud 715 may be comprised of an overmolded protrusion which is adjacent to the housing of the connector. For example, the female connector 702-702" may include the shroud 715 at the planar side of the housing 719.

Figure 13B:
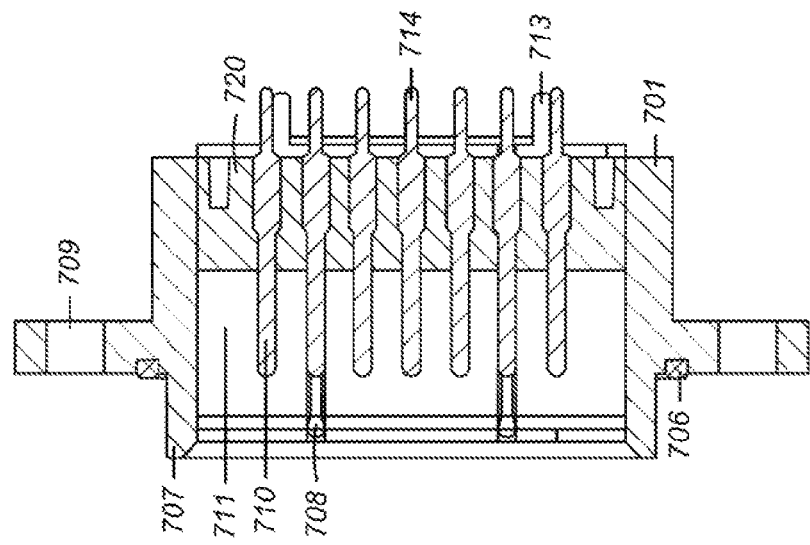
FIGS. 13A-13D are various views of an exemplary implementation of the male connector 701.
Figure 13A:
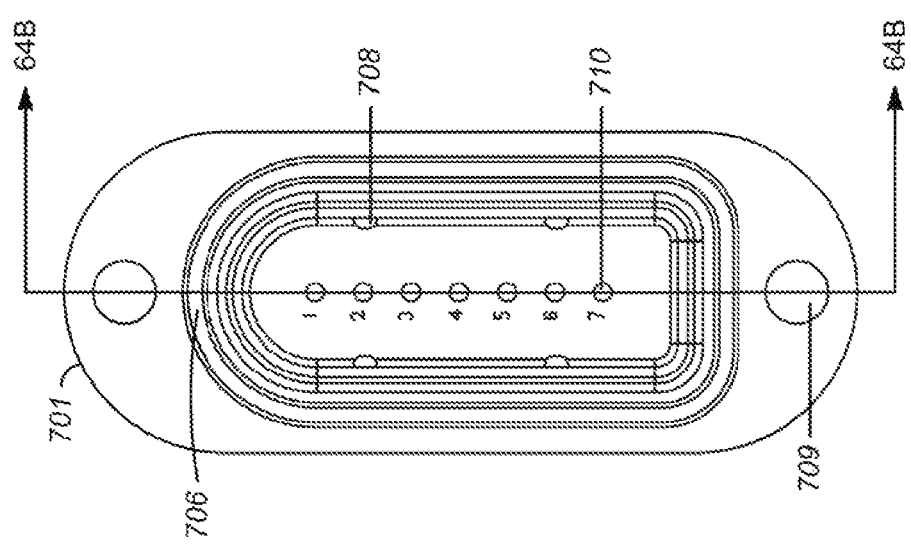
Figure 13D:
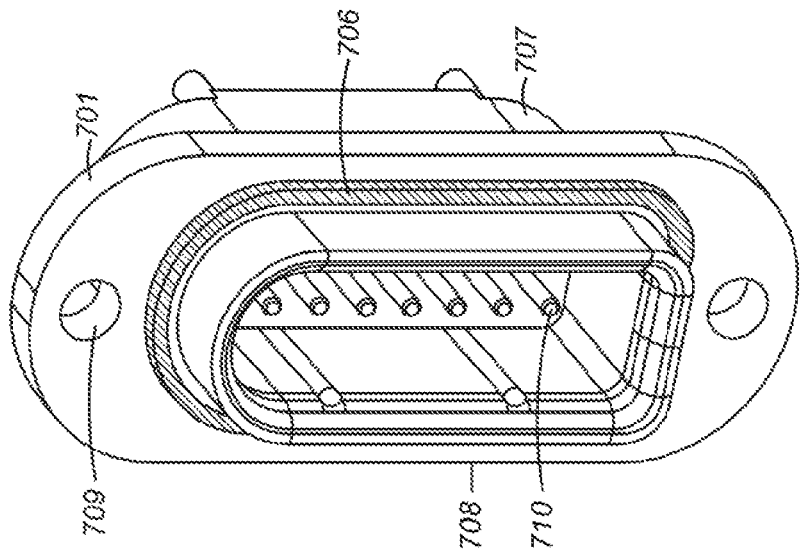
Figure 13C:
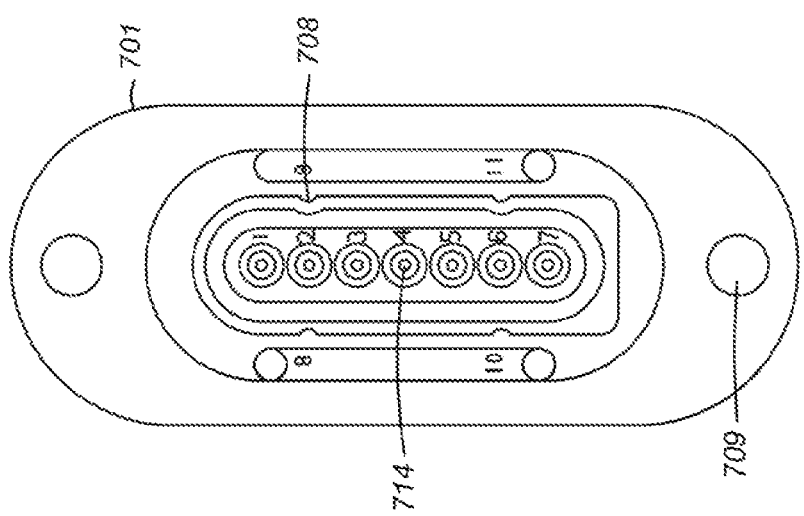
Figure 14B:
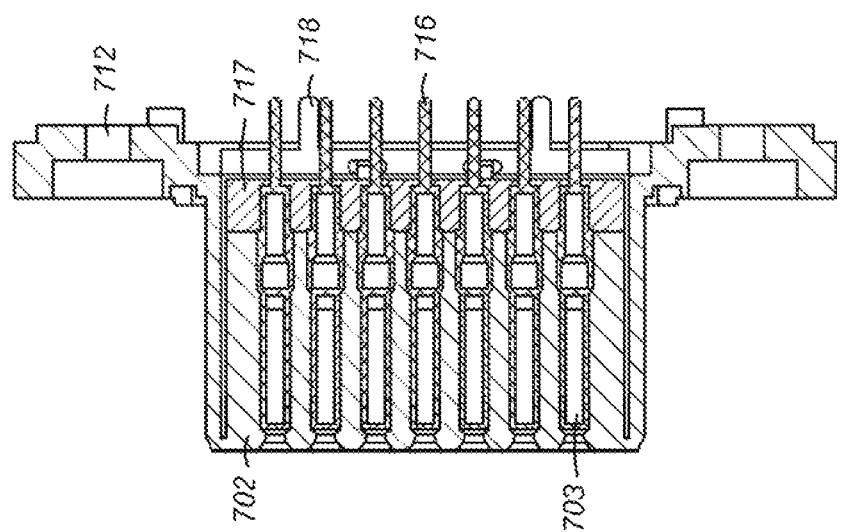
FIGS. 14A-14D are various views of an exemplary implementation of the female connector 702.
Figure 14A:
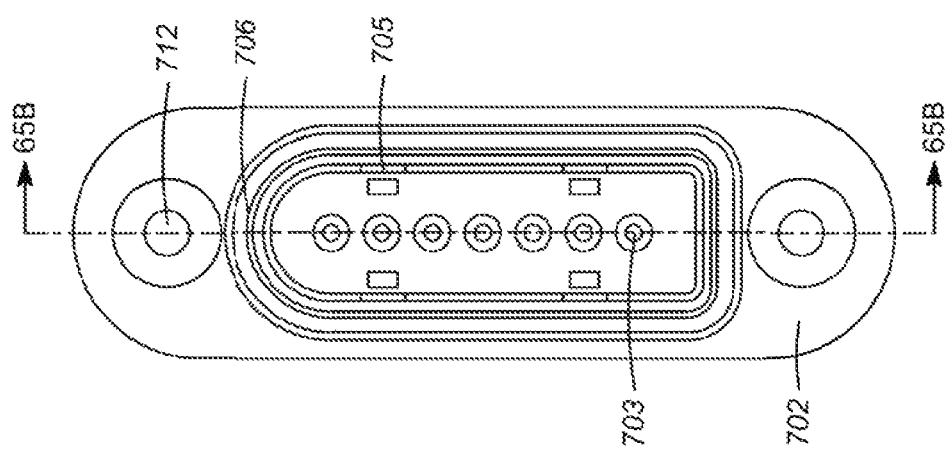
Figure 14D:
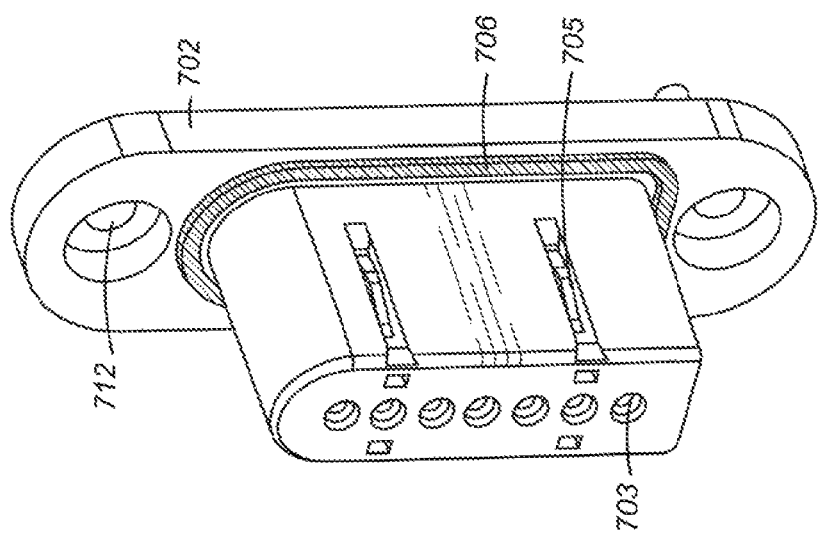
Figure 14C:
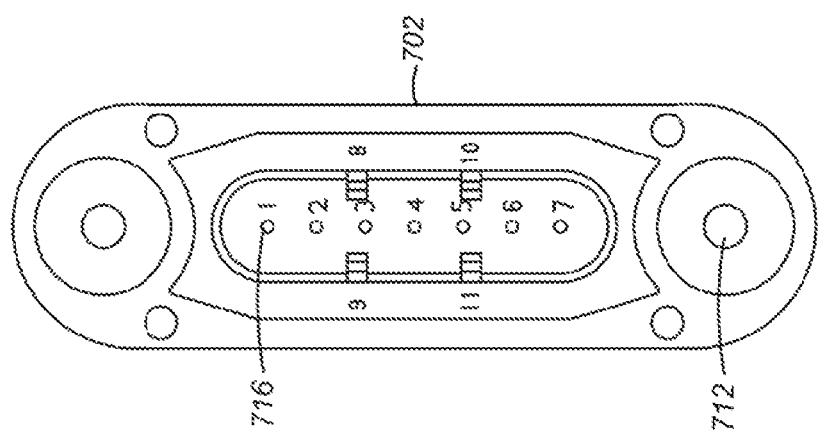

In addition, as shown in FIGS. 13B and 14B, for example, the male connector 701-701" or the female connector 702-702"" may include additional features such as a contact holder 720, a socket holder 717, shield tabs 713, etc. A back face of the male connector 701-701" may include a harness 714 for further electrical or mechanical connection. Similarly, a back face of the female connector 702-702"" may also include a harness 716 for further electrical or mechanical connection.

Figure 17A:
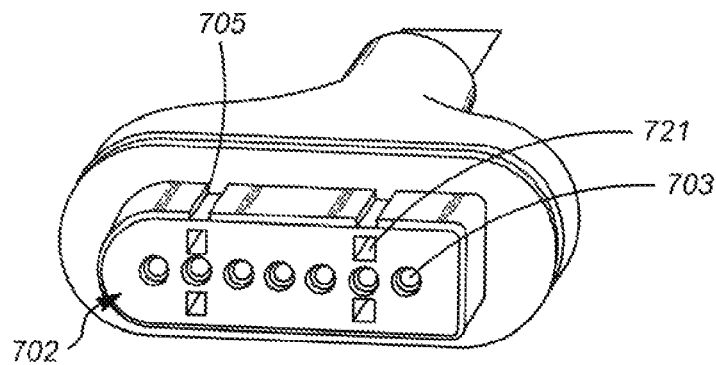
FIGS. 17A-17C are perspective views of exemplary implementations of the female connector 702' and 702".
Figure 17B:
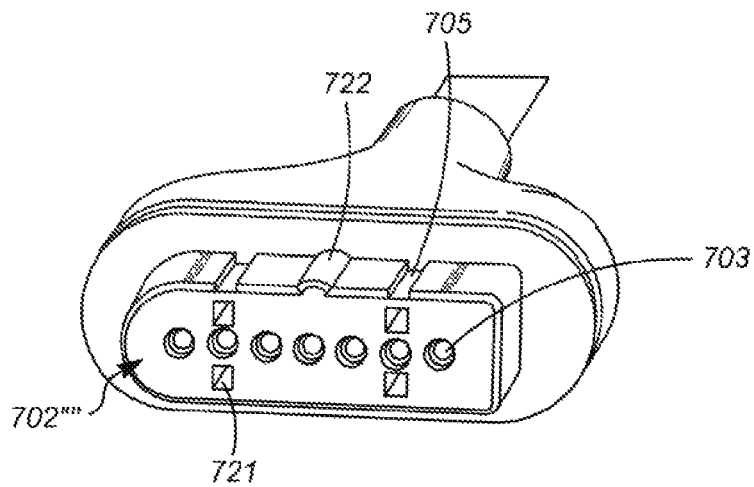
Figure 17C:
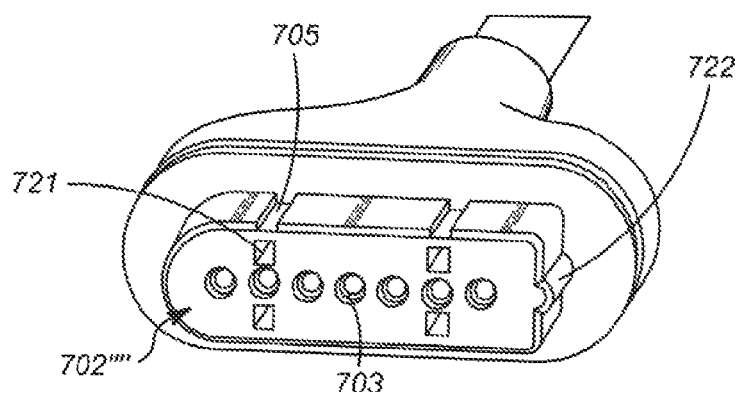
Figure 17D:
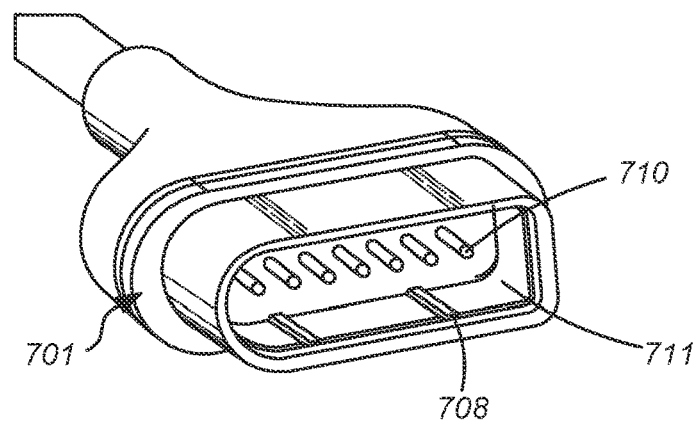
FIGS. 17D-17F are perspective views of exemplary implementations of the male connector 701, 701".

In the embodiments shown in FIGS. 17B and 17C, the female connector 702"" includes at least one shield protrusion 722 formed thereon. The shield protrusion 722 can be formed on one of the longitudinal sides, the rounded side, and/or the planar side of the female connector 702"". In the embodiments shown in FIGS. 17B and 17C, the at least one shield protrusion 722 is rounded.

Alternatively, in embodiments not shown, the male connector 701-701" may include a shroud 715 at the planar side of the housing 707.

Figure 17E:
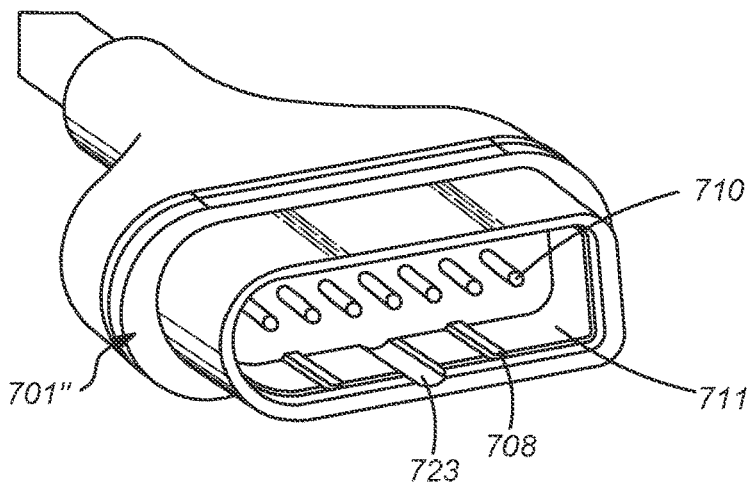
Figure 17F:
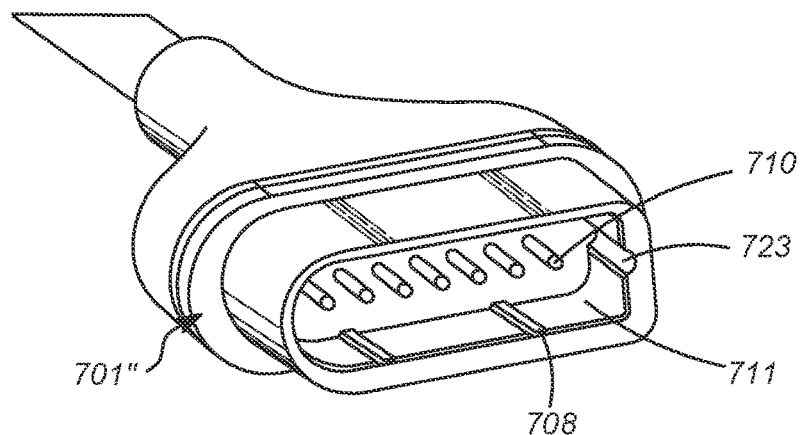

In the embodiments shown in FIGS. 17E and 17F, the male connector 701" includes at least one shield groove 723 formed therein. The shield groove 723 can be formed in one of the longitudinal sides, the rounded side, and/or the planar side of the male connector 701". The shield groove 723 corresponds to and is configured to receive the shield protrusion 722 when the male connector 701" and the female connector 702"" are physically connected. The combination of the shield protrusion 722 and the shield groove 723 ensures that the connectors cannot be inserted into incorrect devices or interfaces. Any of the female connectors 702-702" may optionally include apertures 721 adjacent to the sockets 703 for facilitating formation of the sockets 703 and/or facilitating fluid drainage from an interior of the female connector 702-702"".

Alternatively, in embodiments not shown, the female connector 702-702"" may include at least one shield groove 723 and the male connector 701-701" may include at least one shield protrusion 722. The shield groove 723 can be formed in one of the longitudinal sides, the rounded side, and/or the planar side of the female connector 702-702"". The shield protrusion 722 can be formed in one of the longitudinal sides, the rounded side, and/or the planar side of male connector 701-701".

Figure 18:
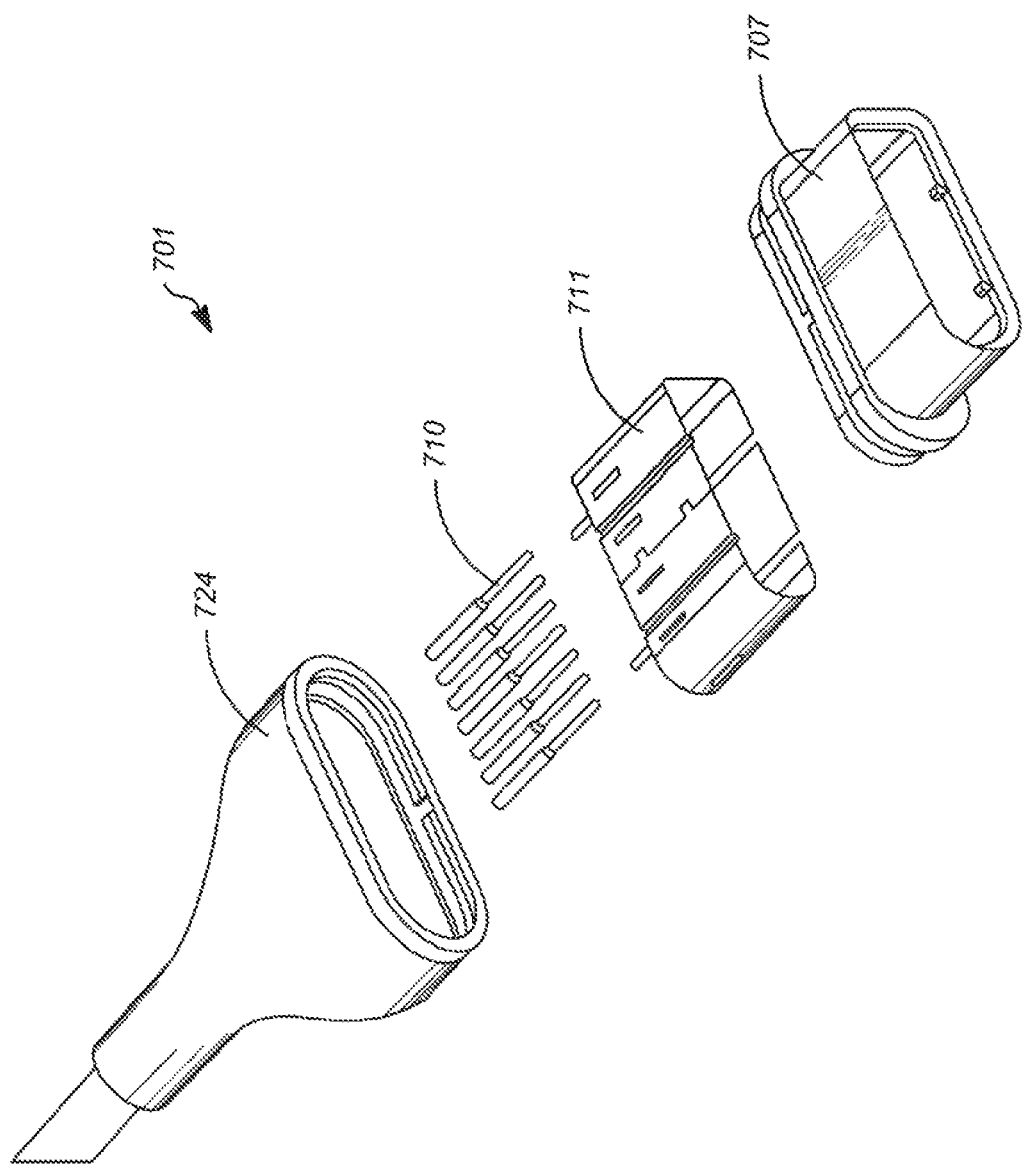
FIG. 18 is an exploded perspective view of an exemplary implementation of the male connector 701.
Figure 19:
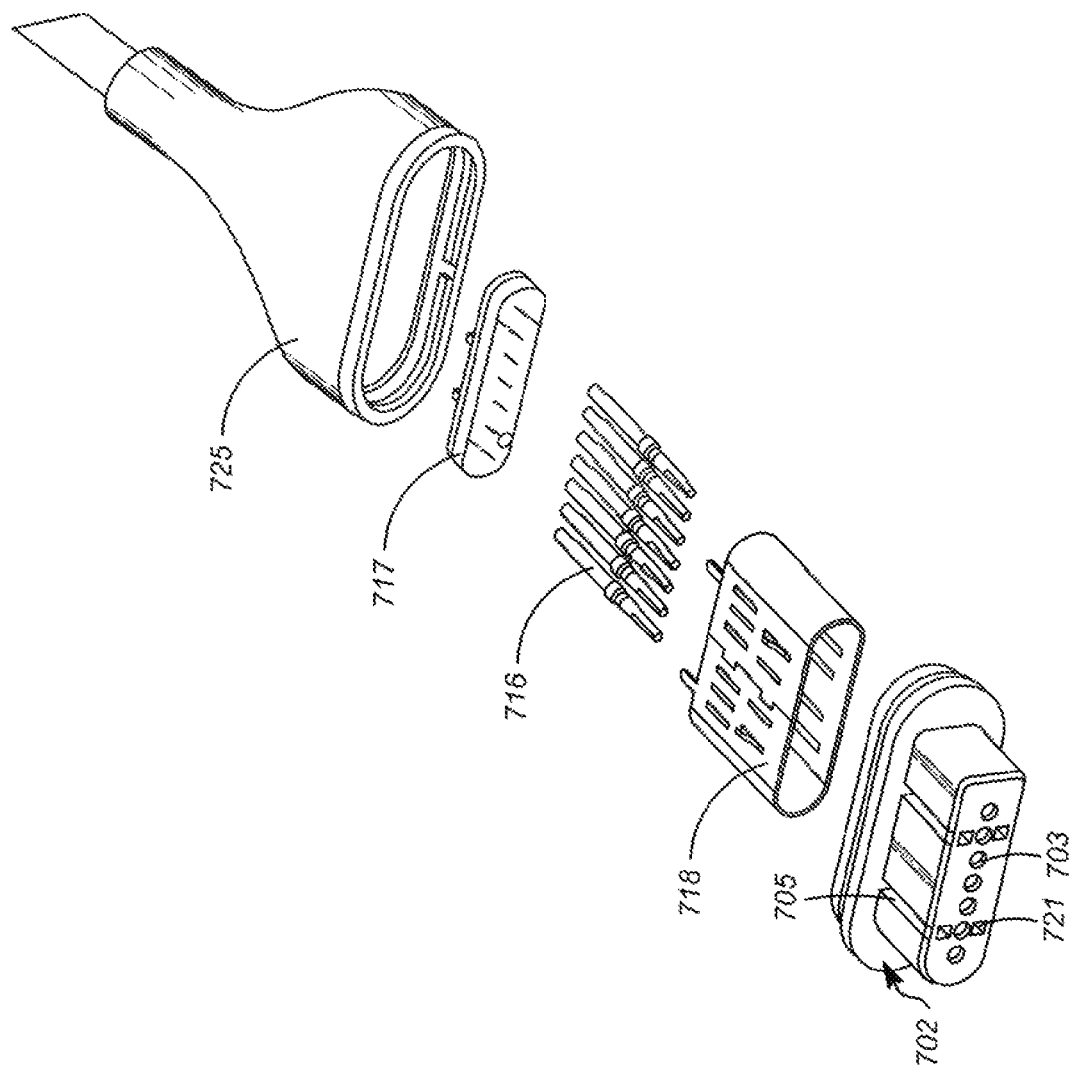
FIG. 19 is an exploded perspective view of an exemplary implementation of the female connector 702.

As shown in FIG. 18, for example, the male connector 701 may include a boot 724 to be attached to an end of a cable. Similarly, as shown in FIG. 19, the female connector 702 may include a boot 725 to be attached to an end of a cable.

Figure 20:
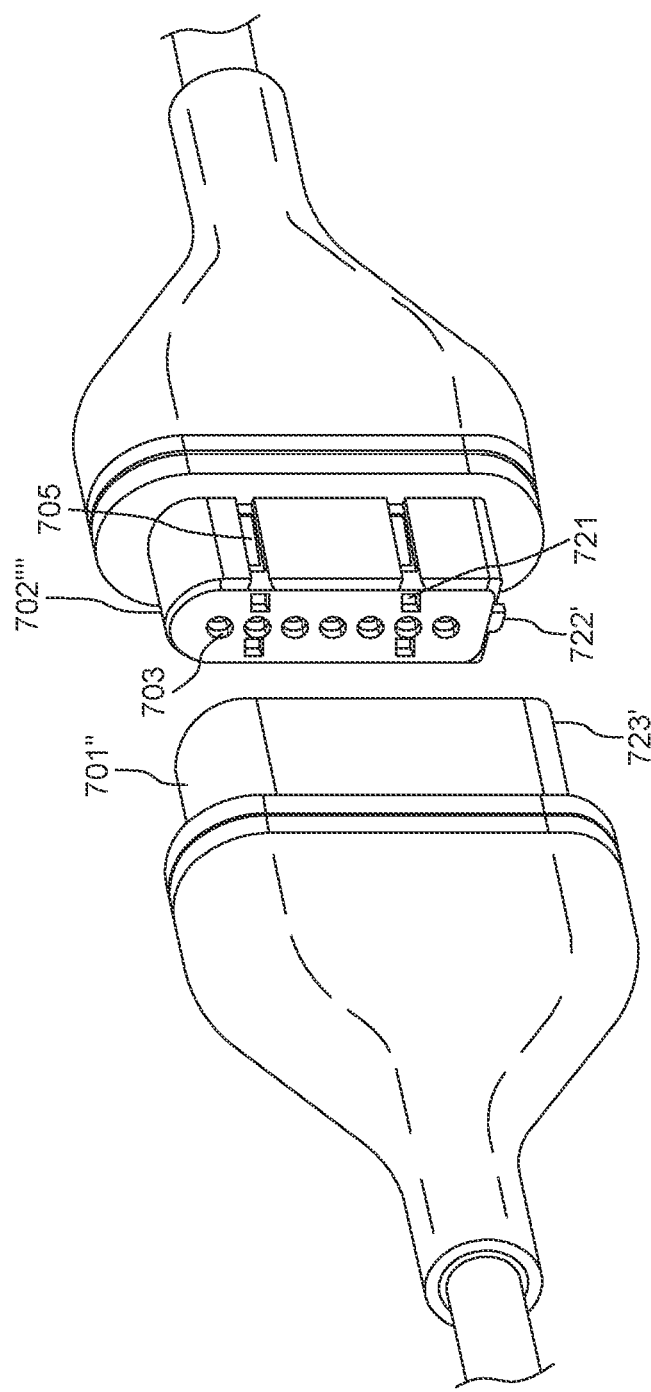
FIG. 20 is an exploded perspective view of an exemplary implementation of the male connector 701" and the female connector 702".
Figure 21:
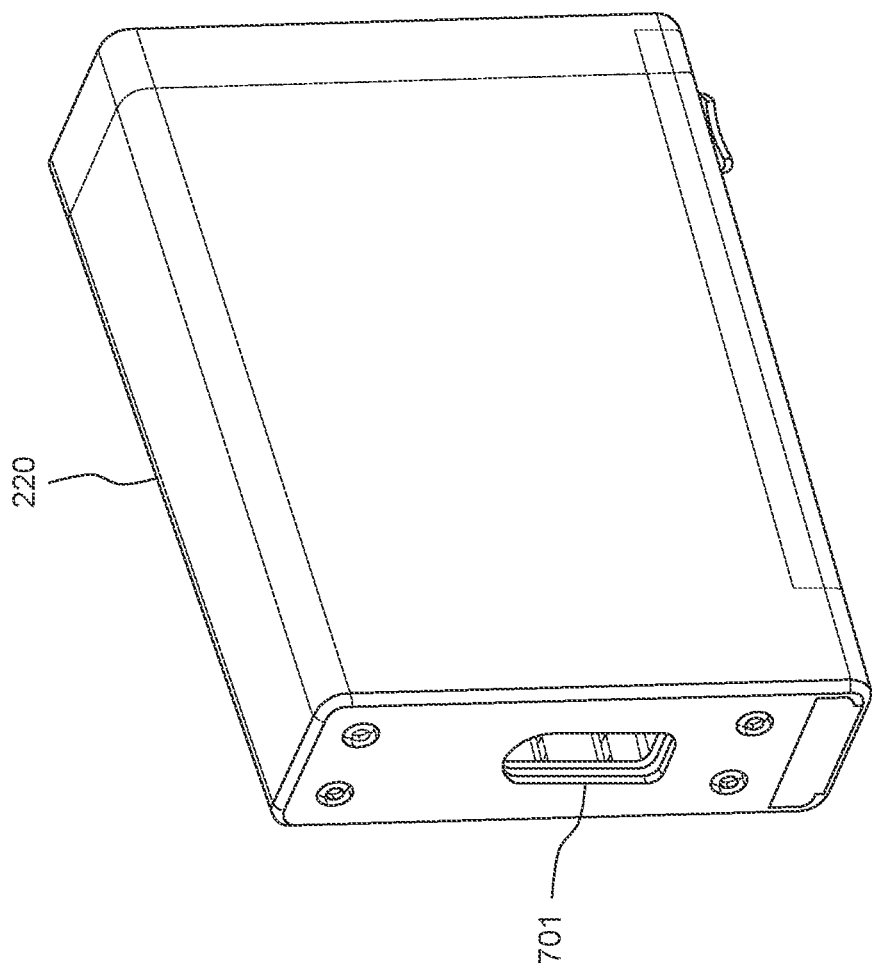
FIG. 21 is an exploded back perspective view of an exemplary system including a rack module 220 and a cable 700.
Figure 21:
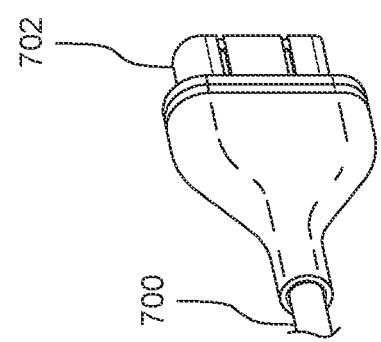

In the embodiment shown in FIG. 20, the female connector 702"" may include at least one shield protrusion 722' formed thereon. In the embodiment shown in FIG. 20, the shield protrusion 722' can be formed on the planar side of the female connector 702" and may be less rounded than the shield protrusion 722 in the embodiment shown in FIG. 17C. The shield protrusion 722' can be, for example, nonround, rectangular, or trapezoidal. In embodiments not shown, the shield protrusion 722' can be formed on one of the longitudinal sides and/or the rounded side of the female connector 702"".

In the embodiment shown in FIG. 20, the male connector 701" may include at least one shield groove 723' formed therein. In the embodiment shown in FIG. 20, the shield groove 723' can be formed in the planar side of the male connector 701" and may be less rounded than the shield groove 723 in the embodiment shown in FIG. 17F. The shield groove 723' can be, for example, nonround, rectangular, or trapezoidal. The shield groove 723' corresponds to and is configured to receive the shield protrusion 722' when the male connector 701" and the female connector 702"" are physically connected. The combination of the shield protrusion 722' and the shield groove 723' ensures that the connectors cannot be inserted into incorrect devices or interfaces.

Exemplary construction materials for various elements of the connector can include 10% GF PBT contact pins, and brass with 10 micro inch gold plating over 150 micro inch nickel plate per ASTM B488 Type 1-C. An exemplary color for various elements of the connector can be RAL 7032. The connector may be rated to have a 10 mOHM current capacity, an initial mating force may be less than 5N and the connector should be able to withstand a minimum of 5000 mate and un-mate cycles such that a change in the contact resistance is no greater than 0.50 mOHM. The connector may also be sealed watertight IP54 minimum between contacts and a PCB therein. Therefore, the connectors 701-702"" have conspicuous keying and external shapes that are asymmetrical and can be felt in low light conditions, are easy to mate with corresponding devices or interfaces, and provide electrical and mechanical connections that can be simply physically or tactually confirmed.

The connector of the present disclosure therefore addresses deficiencies of inconspicuous keying and difficulty in mating with corresponding interfaces, and the requirement of painstaking visual confirmation of the orientations of the interfaces in order to ensure a proper connection.

Any feature of any particular portion, embodiment or modification of the connector 701-702" may be included or omitted from any of the other portions, embodiments or modifications of the connector 701-702"".

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and a server are generally remote from each other and typically interact through a communication network. The relationship of the client and the server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as, for example, magnetic disks, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as, for example, as would a non-transient solid-state memory or a magnetic hard drive or any equivalent storage medium. The machine-readable medium can alternatively or additionally store such machine instructions in a transient manner, such as, for example, as would a processor cache or other random access memory associated with one or more physical processor cores.

To provide for interaction with a user, one or more aspects or features of the subject matter described herein can be implemented on a computer having a display device, such as, for example, a cathode ray tube (CRT) or a liquid crystal display (LCD) or a light emitting diode (LED) monitor for displaying information to the user and a keyboard and a pointing device, such as, for example, a mouse or a trackball, by which the user may provide input to the computer. Other kinds of devices can be used to provide for interaction with a user as well. For example, feedback provided to the user can be any form of sensory feedback, such as, for example, visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

It is also contemplated that the implementation of the components of the present disclosure can be done with any newly arising technology that may replace any of the above implementation technologies.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, the implementations set forth in the foregoing description are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. An apparatus comprising:
a female connector including a first housing, a first top end, a first bottom end, a first longitudinal side and a second longitudinal side, a front surface, and a plurality of sockets, the first longitudinal side being parallel to the second longitudinal side, the first bottom end being planar and connecting the first and second longitudinal sides, the first top end being rounded and connecting the first and second longitudinal sides, the first top end being distal to the first bottom end, the plurality of sockets being located in the front surface and arranged along a first line parallel to the first and second longitudinal sides, wherein the female connector further comprises at least first and second apertures being located in the front surface and arranged along a second line parallel to the first line, the second line situated between the first line and the first longitudinal side, and third and fourth apertures formed in the front surface and arranged along a third line parallel to the first line, the third line situated between the first line and the second longitudinal side, the first, second, third, and fourth apertures arranged for draining fluid from within an interior of the first housing.

2. The apparatus of claim 1, further comprising a male connector including a second housing, a second top end, a second bottom end, a third longitudinal side, a fourth longitudinal side and a plurality of pins, the third longitudinal side being parallel to the fourth longitudinal side, the second bottom end being planar and connecting the third and fourth longitudinal sides, the second top end being rounded and connecting the third and fourth longitudinal sides, the second top end being distal to the second bottom end, the second top end, the second bottom end, the third longitudinal side, and the fourth longitudinal side defining a front recess that extends rearwardly to a recessed surface, the plurality of pins extending forwardly from the recessed surface and being arranged along a fourth second line parallel to the third and fourth longitudinal side;

wherein the first housing is configured to be insertable into the recess of the second housing so that the plurality of pins enter into the plurality of sockets.

3. The apparatus of claim 1, wherein the female connector further comprises at least one shield protrusion formed on the housing thereof, the shield protrusion projecting outwardly from the housing.

4. The apparatus of claim 1, wherein the first and third apertures are arranged along a fifth line that is perpendicular to the first and second longitudinal sides, and wherein the second and fourth apertures are arranged along a sixth line that is perpendicular to the first and second longitudinal sides.

5. The apparatus of claim 4, wherein the plurality of sockets comprises a first socket and a last socket and wherein the first and third apertures are aligned with a socket positioned adjacent the first socket, and wherein the second and fourth apertures are aligned with a socket positioned adjacent to the last socket.

6. The apparatus of claim 4, wherein the first, second, third, and fourth apertures are rectangular in shape.

7. The apparatus of claim 4, wherein the first longitudinal side has a first shield spring and the second longitudinal side has a second shield spring, the first and second shield springs being aligned with the fifth line.

8. The apparatus of claim 1, wherein the first housing further comprises a shield protrusion extending outwardly therefrom.

9. The apparatus of claim 1, wherein the first housing comprises a shroud that is adjacent to and spaced apart from the first bottom end.

10. The apparatus of claim 1, additionally comprising a gasket including a rounded end positioned adjacent the first top end of the first housing and a planar end positioned adjacent the first bottom end of the first housing.

11. The apparatus of claim 10, wherein the gasket additionally comprises elongate sides connecting the rounded and planar ends of the gasket.

12. The apparatus of claim 11, wherein the elongate sides of the gasket are positioned adjacent the first and second longitudinal sides of the first housing.

13. The apparatus of claim 1, wherein the front surface comprises a socket holder for retaining the plurality of sockets therein.

14. The apparatus of claim 1, additionally comprising a boot arranged for attachment to an end of a cable, the boot arranged for connecting with the female connector.

15. The apparatus of claim 10, additionally comprising a mounting flange on which the housing is positioned, wherein the gasket is affixed to the mounting flange.

16. The apparatus of claim 15, wherein the mounting flange includes holes sized for receiving fasteners.

17. The apparatus of claim 1, wherein the first, second, third, and fourth apertures are non-round in shape.

18. An apparatus comprising:

a male connector including a male connector housing, a top end, a bottom end, a first longitudinal side, a second longitudinal side and a plurality of pins, the first longitudinal side being parallel to the second longitudinal side, the bottom end being planar and connecting the first and second longitudinal sides, the top end being rounded and connecting the first and second longitudinal sides, the top end being distal to the bottom end, the top end, the bottom end, the first longitudinal side, and the second longitudinal side defining a front recess that extends rearwardly to a recessed surface, the plurality of pins extending forwardly from the recessed surface and being arranged along a second line parallel to the first and second longitudinal sides;

wherein the male connector additionally comprises a gasket surrounding the male connector housing, the gasket including a rounded end positioned adjacent the first top end of the first housing and a planar end positioned adjacent the first bottom end of the first housing;

wherein the recess of the male connector housing is arranged to receive a plurality of sockets of a female connector so that the plurality of pins of the male connector housing enters into the plurality of sockets; and, wherein the male connector additionally comprises a shield extending 360 degrees about the male connector housing, the shield including at least two shield protrusions and a shield groove, the shield groove situated between the at least two shield protrusions, wherein each of the at least two shield protrusions projects inwardly, and the shield groove projects outwardly.

19. The apparatus of claim 18, wherein the gasket additionally comprises elongate sides connecting the rounded and planar ends of the gasket.

* * * * *